(12) United States Patent
Kapadia et al.

(10) Patent No.: US 11,944,510 B2
(45) Date of Patent: Apr. 2, 2024

(54) ROBOTIC SURGICAL SYSTEMS AND ROBOTIC ARM CARTS THEREOF

(71) Applicant: Covidien LP, Mansfield, MA (US)

(72) Inventors: Jaimeen Kapadia, Cambridge, MA (US); Shane Reardon, Branford, CT (US)

(73) Assignee: COVIDIEN LP, Mansfield, MA (US)

( * ) Notice: Subject to any disclaimer, the term of this patent is extended or adjusted under 35 U.S.C. 154(b) by 840 days.

(21) Appl. No.: 17/047,788

(22) PCT Filed: Mar. 28, 2019

(86) PCT No.: PCT/US2019/024509
§ 371 (c)(1),
(2) Date: Oct. 15, 2020

(87) PCT Pub. No.: WO2019/203999
PCT Pub. Date: Oct. 24, 2019

(65) Prior Publication Data
US 2021/0153973 A1      May 27, 2021

Related U.S. Application Data

(60) Provisional application No. 62/658,101, filed on Apr. 16, 2018.

(51) Int. Cl.
*H05G 1/02*      (2006.01)
*A61B 34/35*     (2016.01)
(Continued)

(52) U.S. Cl.
CPC .............. *A61B 90/50* (2016.02); *A61B 34/35* (2016.02); *A61B 50/13* (2016.02); *B25J 5/007* (2013.01);
(Continued)

(58) Field of Classification Search
CPC ......... A61B 90/50; A61B 34/35; A61B 50/13; A61B 2090/504; A61B 2090/508; B25J 9/104; B25J 19/002
See application file for complete search history.

(56) References Cited

U.S. PATENT DOCUMENTS

| 6,441,577 B2 | 8/2002 | Blumenkranz et al. |
| 8,808,278 B2 | 8/2014 | Goldberg et al. |

(Continued)

FOREIGN PATENT DOCUMENTS

| CN | 103896183 B | 8/2016 |
| EP | 2957272 A1 | 12/2015 |

(Continued)

OTHER PUBLICATIONS

International Search Report dated Jul. 8, 2019, issued in international application PCT/US2019/024509, 3 pages.

(Continued)

*Primary Examiner* — Muhammad S Islam
(74) *Attorney, Agent, or Firm* — Carter, DeLuca & Farrell, LLP

(57) ABSTRACT

A surgical cart for supporting a robotic arm includes a vertically-extending support column, a carriage movably coupled to the support column and configured to carry a robotic arm, and a braking mechanism.

24 Claims, 20 Drawing Sheets

(51) Int. Cl.
    *A61B 50/13*     (2016.01)
    *A61B 90/50*     (2016.01)
    *B25J 5/00*     (2006.01)
    *B25J 9/10*     (2006.01)
    *B25J 19/00*     (2006.01)

(52) U.S. Cl.
    CPC ........... *B25J 9/104* (2013.01); *B25J 19/0004* (2013.01); *B25J 19/002* (2013.01); *A61B 2090/504* (2016.02); *A61B 2090/508* (2016.02)

(56) References Cited

U.S. PATENT DOCUMENTS

| | | |
|---|---|---|
| 10,034,721 B1 | 7/2018 | Timm et al. |
| 2007/0029142 A1 | 2/2007 | Drennen et al. |
| 2009/0024142 A1 | 1/2009 | Ruiz Morales |
| 2010/0163694 A1 | 7/2010 | Fadler et al. |
| 2011/0249805 A1 | 10/2011 | Kralles et al. |
| 2015/0217446 A1 | 8/2015 | Kremerman |
| 2016/0158932 A1* | 6/2016 | Wyrobek ............ B25J 5/007 180/21 |

FOREIGN PATENT DOCUMENTS

| | | |
|---|---|---|
| JP | 6469304 B1 | 2/2019 |
| WO | 0179103 A1 | 10/2001 |
| WO | 2015142784 A1 | 9/2015 |

OTHER PUBLICATIONS

Extended European Search Report dated Oct. 21, 2022 corresponding to counterpart Patent Application EP 20759973.9.
European Search Report dated Dec. 14, 2021, issued in corresponding EP Appln. No. 19789524, 14 pages.

* cited by examiner

ROBOTIC SURGICAL SYSTEMS AND ROBOTIC ARM CARTS THEREOF

BACKGROUND

Robotic surgical systems are used in minimally invasive medical procedures because of their increased accuracy and expediency relative to handheld surgical instruments. In these robotic surgical systems, a robotic arm supports a surgical instrument having an end effector mounted thereto by a wrist assembly. In operation, the robotic arm is moved to a position over a patient and then guides the surgical instrument into a small incision via a surgical port or a natural orifice of a patient to position the end effector at a work site within the patient's body.

Typically, a cart is provided to support the robotic arm and allow a clinician to move the robotic arm to different locations within the operating room. The height of the robotic arm over a patient may need to be adjusted (e.g., the robotic arm is lowered or raised) to precisely position the end effector at a work site within a patient's body. Adjusting the height of the robotic arm involves moving the robotic arm vertically along a support column of the cart. Due to the weight of the robotic arm and/or other components associated with the robotic arm, manual adjustment of the vertical position of the robotic arm may require a lot of force applied either manually or by a motor.

Accordingly, solutions are sought for overcoming the challenges involved in adjusting the height of a robotic arm. In addition, there is room for improving the mechanisms used in maintaining the robotic arm at the selected height.

SUMMARY

In accordance with an embodiment of the present disclosure,

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
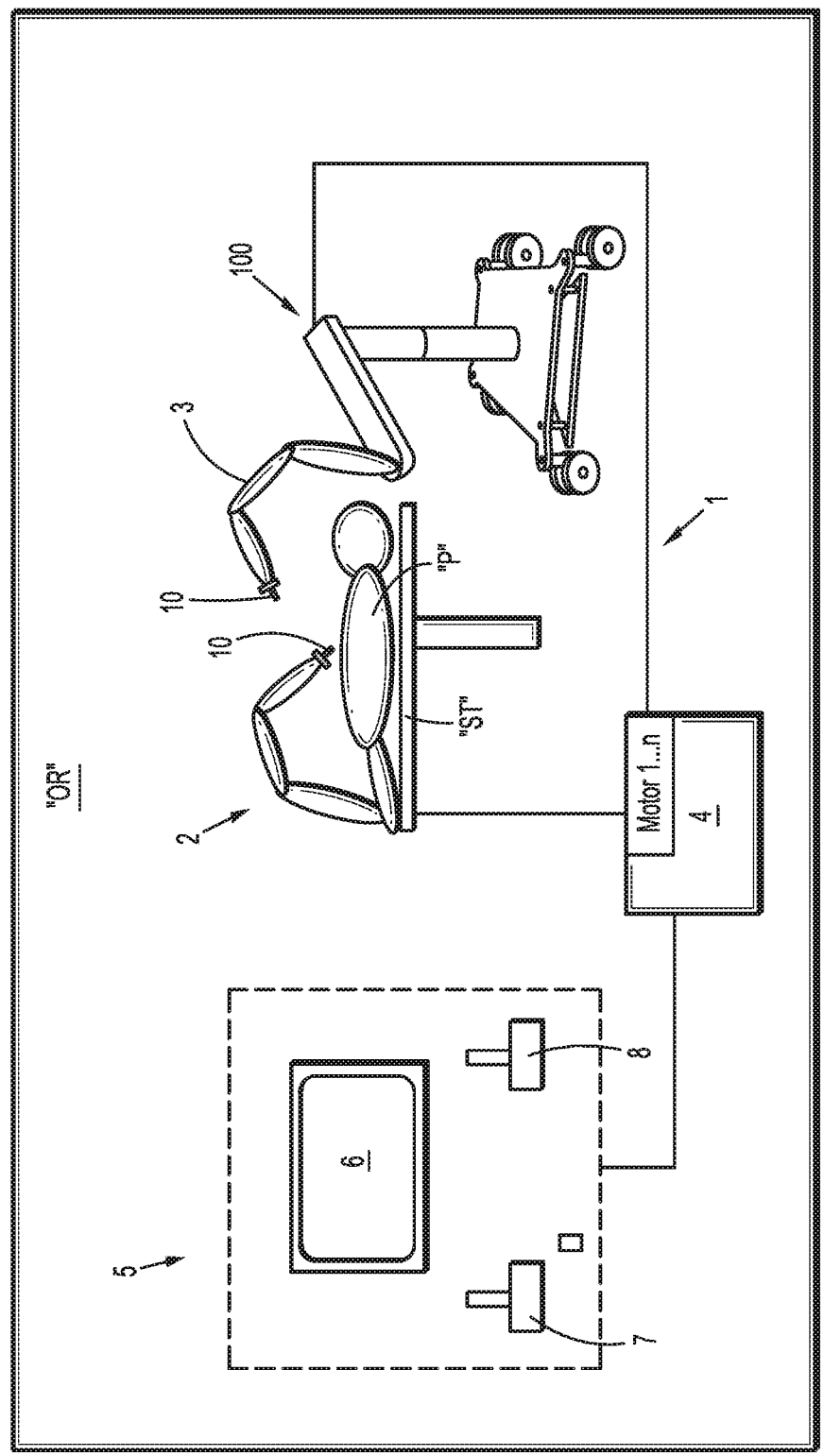
FIG. 1 is a schematic illustration of a robotic surgical system including a surgical cart in accordance with the present disclosure.

Embodiments of the presently disclosed robotic surgical systems including various embodiments of a robotic arm cart and methods of use thereof are described in detail with reference to the drawings, in which like reference numerals designate identical or corresponding elements in each of the several views. As used herein the term "distal" refers to that portion of the robotic surgical system or component thereof, that is closer to the patient, while the term "proximal" refers to that portion of the robotic surgical system or component thereof, that is farther from the patient.

As will be described in detail below, provided are embodiments of a surgical cart for supporting a robotic arm and for facilitating movement of the robotic arm around an operating room. The cart includes a base equipped with wheels, and a support column extending vertically from the base. The support column supports a carriage that is movable along the vertical axis of the support column and which carries a robotic arm. The surgical cart further includes a counterbalance mechanism that functions to assist a clinician in manually adjusting the vertical position of the carriage along the support column. Further provided by the present disclosure is a braking mechanism that maintains the selected vertical position of the carriage relative to the support column.

Referring initially to FIG. 1, a surgical system, such as, for example, a robotic surgical system 1 is shown. In embodiments, robotic surgical system 1 is located in an operating room "OR." Robotic surgical system 1 generally includes a plurality of surgical robotic arms 2, 3 having a surgical instrument, such as, for example, an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), e.g., a clinician, is able to telemanipulate robotic arms 2, 3 in a first operating mode, as known in principle to a person skilled in the art. Each of the robotic arms 2, 3 may be composed of a plurality of members, which are connected through joints.

Robotic arms 2, 3 may be driven by electric drives (not shown) that are connected to control device 4. Control device 4 (e.g., a computer) is set up to activate the drives, in particular by means of a computer program, in such a way that robotic arms 2, 3 and thus electromechanical instrument 10 (including the electromechanical end effector (not shown)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more or less than two robotic arms 2, 3, the additional robotic arms likewise being connected to control device 4 and being telemanipulatable by means of operating console 5. A surgical instrument, for example, electromechanical instrument 10 (including the electromechanical end effector), may also be attached to the additional robotic arm.

The robotic arms, such as for example, robotic arm 3, is supported on a surgical cart 100. The surgical cart 100 may incorporate the control device 4. In embodiments, the robotic arms, such as for example, robotic arm 2 may be coupled to the surgical table "ST."

For a detailed discussion of the construction and operation of a robotic surgical system, reference may be made to U.S. Pat. No. 8,828,023, entitled "Medical Workstation," the entire content of which is incorporated herein by reference.

Figure 2:
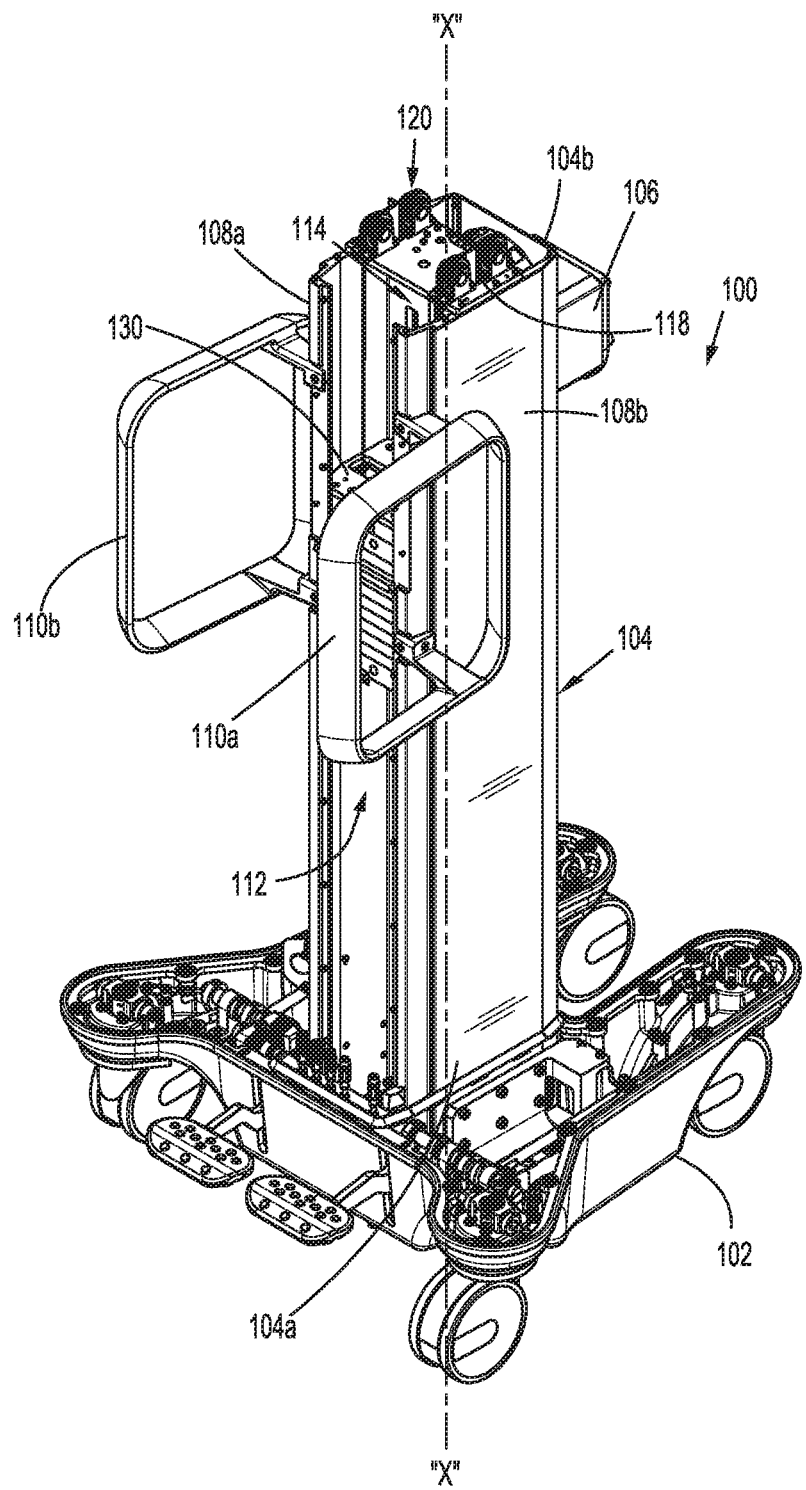
FIG. 2 is a rear, perspective view of one embodiment of a surgical cart of the robotic surgical system of FIG. 1.

With reference to FIG. 2, one exemplary embodiment of a surgical cart of robotic surgical system 1, configured for use in accordance with the present disclosure, is shown generally using reference numeral 100. The surgical cart 100 is configured to move robotic arm 3 (FIG. 1) to a selected position within operating room "OR" (FIG. 1) and to provide height adjustment of the robotic arm 3. The surgical cart 100 generally includes a cart base 102, a support column 104 extending vertically (i.e., perpendicularly) from the cart base 102, and a carriage or slider 106 slidably supported on column 104 and configured for supporting robotic arm 3 thereon.

The support column 104 of the surgical cart 100 defines a longitudinal axis "X" and has a first end 104a supported on the cart base 102 and a second free end 104b. The support column 104 includes a pair of opposed sidewalls 108a, 108b. A pair of handles 110a, 110b is attached to respective sidewalls 108a, 108b and is configured to be grasped by a clinician to facilitate movement of the surgical cart 100 within the operating room "OR." The sidewalls 108a, 108b of the support column 104 are laterally spaced from one another to define a longitudinally-extending channel 112 having an internal support structure 114 disposed therein.

Figure 3:
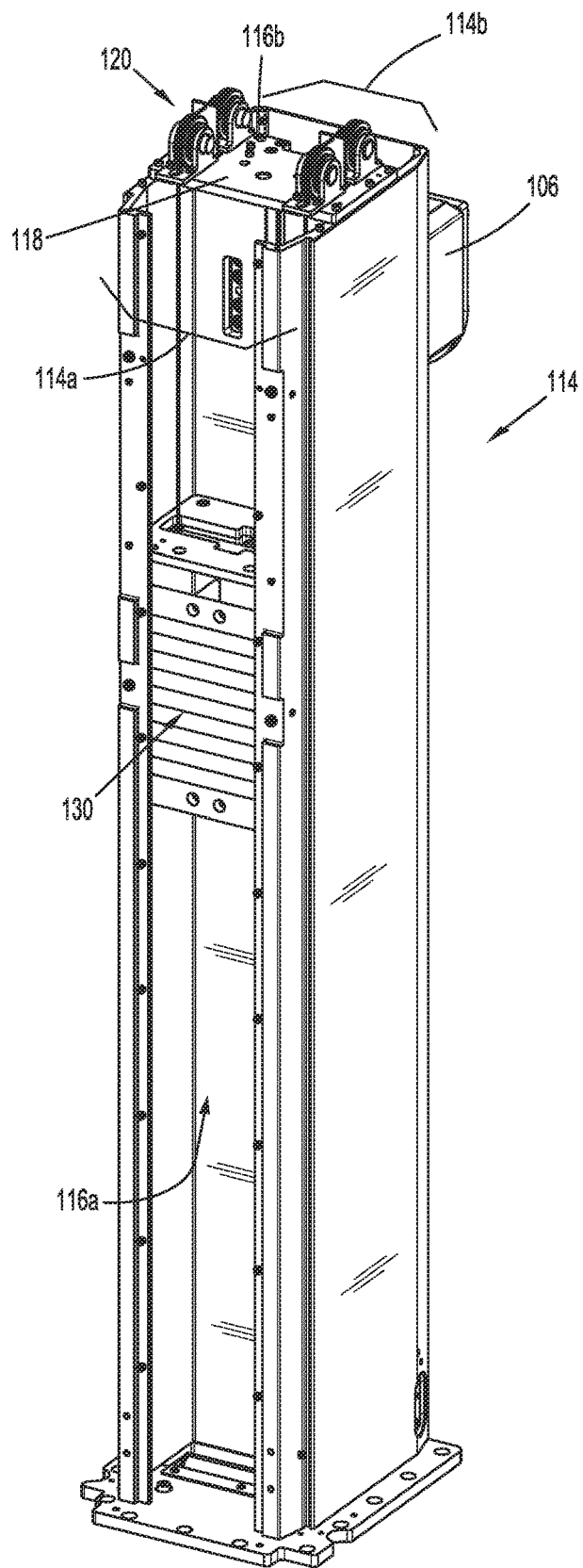
FIG. 3 is a perspective view of a pulley assembly disposed within a support column of the surgical cart of FIG. 2.

With reference to FIGS. 2 and 3, the internal support structure 114 of the support column 104 extends along the longitudinal axis "X" of the support column 104 and is configured to slidably support both the carriage 106 and a counterweight 130. In particular, the internal support structure 114 of the support column 104 has a first longitudinal side 114a defining a first longitudinally-extending track 116a, and a second longitudinal side 114b defining a second longitudinally-extending track 116b. The carriage 106 is slidably supported in the first track 116a of the first longitudinal side 114a, and the counterweight 130 is slidably supported in the second track 116b of the second longitudinal side 114b. The support column 104 includes a platform 118 disposed on the internal support structure 114, at second free end 104b of column 104, for supporting a pulley assembly 120 thereon.

Figure 4:
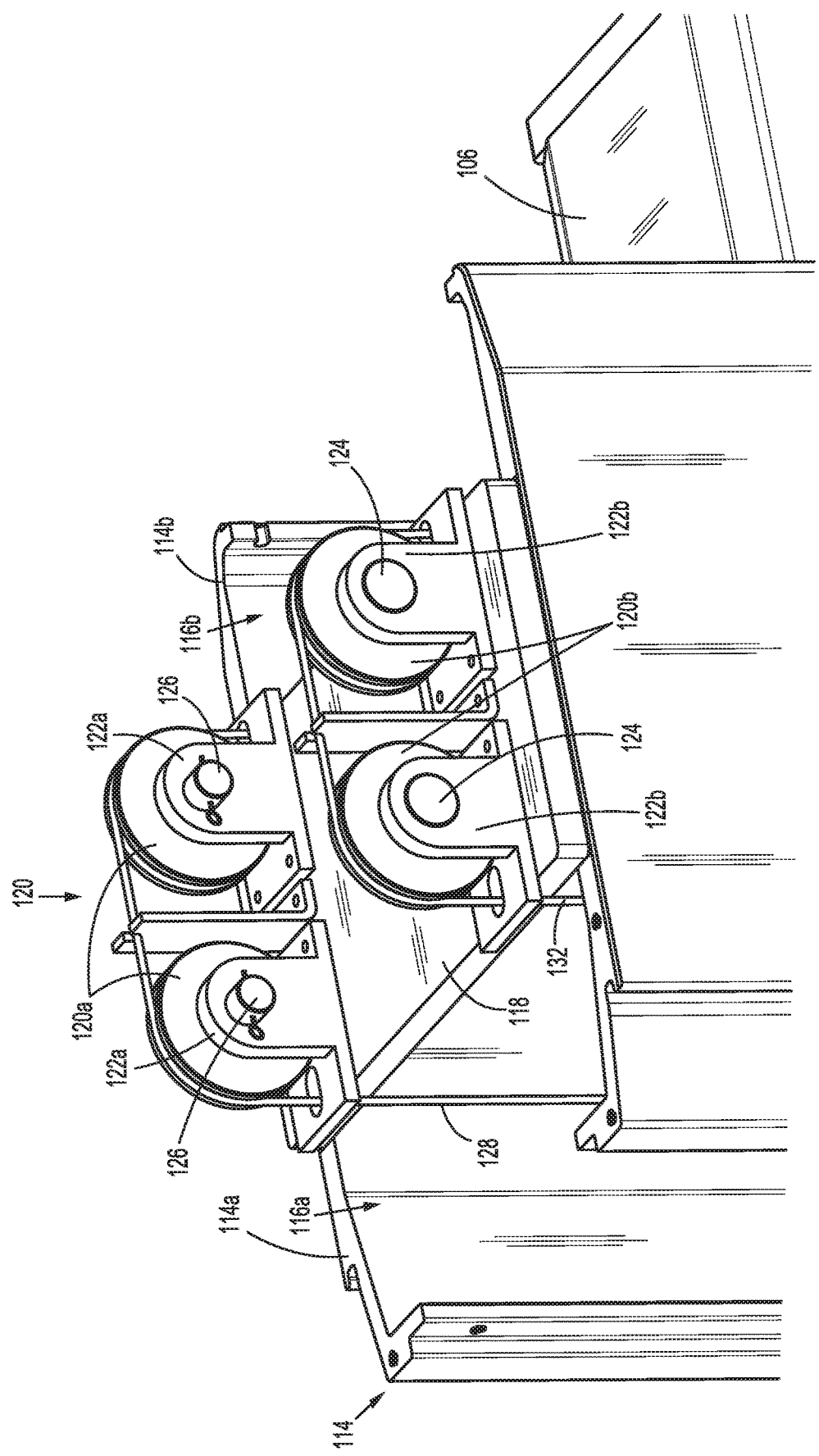
FIG. 4 is an enlarged, perspective view of the pulley assembly of FIG. 3.
Figure 5:
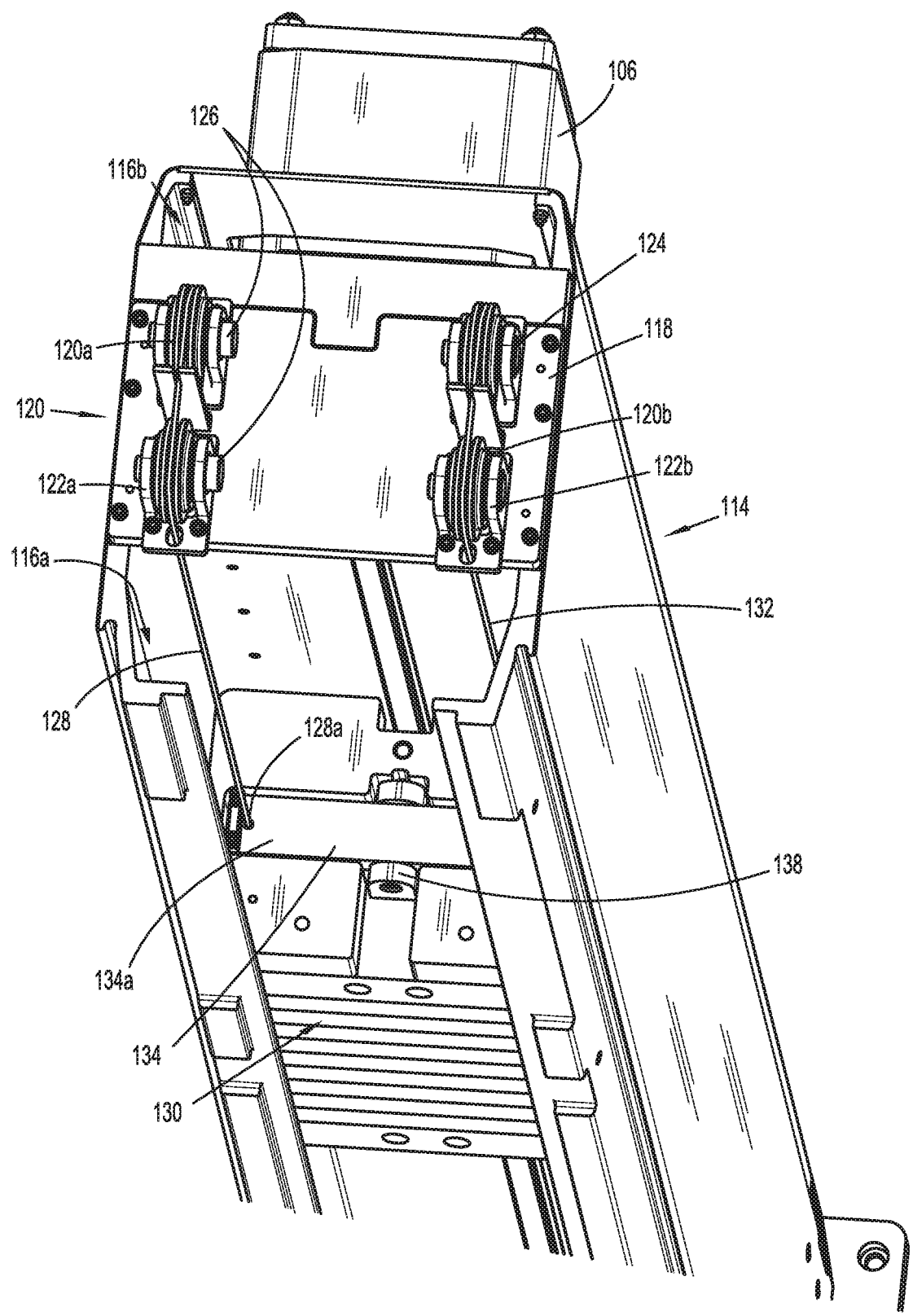
FIG. 5 is a top, perspective view of the pulley assembly of FIG. 3 coupled to a counterweight.

With reference to FIGS. 4 and 5, surgical cart 100 includes the pulley assembly which mechanically joins the carriage 106 with the counterweight 130. The pulley assembly 120 includes a first pair of pulleys 120a and a second pair of pulleys 120b each supported on and fixed to the platform 118 of the support column 104. The first and second pairs of pulleys 120a, 120b are spaced laterally from one another such that the first pair of pulleys 120a is disposed adjacent the first sidewall 108a (FIG. 2) of the support column 104, and the second pair of pulleys 120b is disposed adjacent the second sidewall 108b (FIG. 2) of the support column 104. It is contemplated that the pulley assembly 120 may include first and second solitary pulleys instead of first and second pairs of pulleys.

The pulleys 120a, 120b are rotatably supported on platform 118 via respective hubs 122a, 122b. It is contemplated that each of the hubs 122a, 122b may include a braking mechanism 124, such as, for example, a servomotor brake or an electromagnetic brake, configured to selectively halt rotation of the pulleys 120a, 120b. In embodiments, the hubs 122a, 122b may each include a motor 126 for driving a rotation of the pulleys 120a, 120b, thereby moving the carriage 106. A detailed description of an exemplary servomotor brake may be found in U.S. Pat. No. 6,273,221, the entire content of which is incorporated by reference herein. In embodiments, the pulleys 120a, 120b may have an absolute encoder to determine a position of the robotic arm 3.

Figure 6:
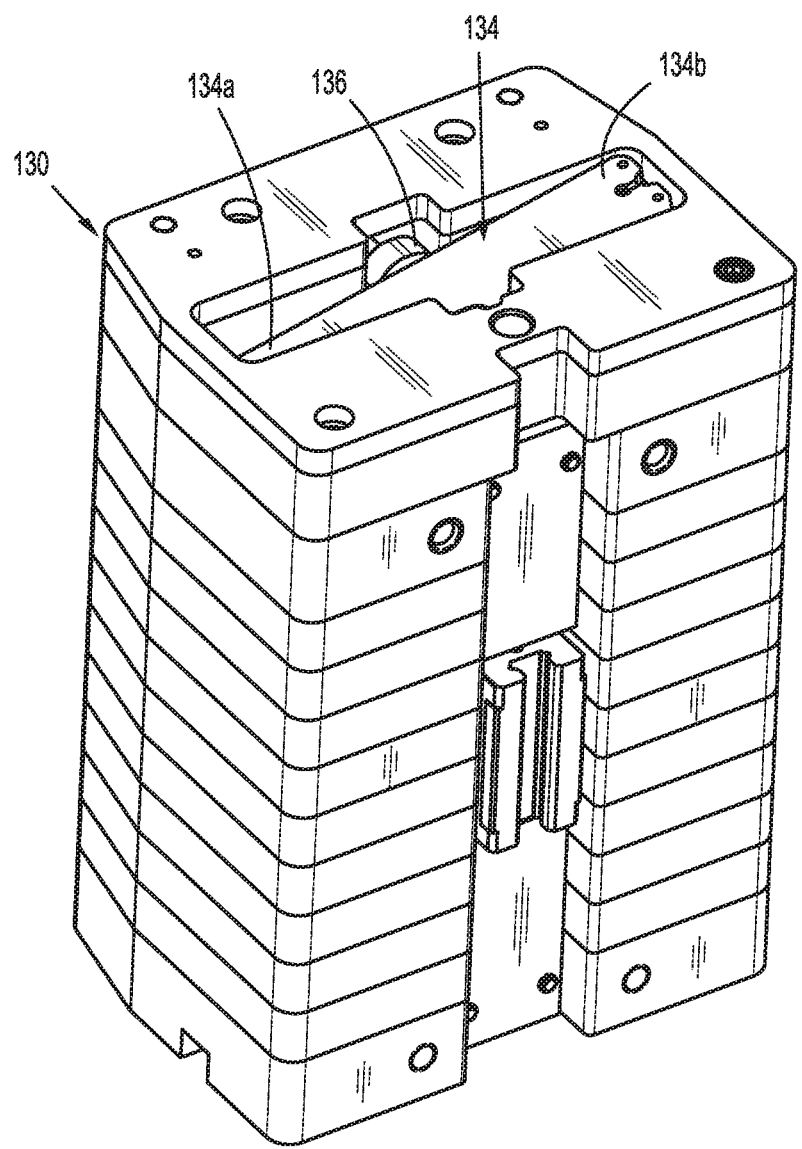
FIG. 6 is a perspective view of the counterweight of FIG. 5.

With reference to FIGS. 5 and 6, the pulley assembly 120 includes first and second cables 128, 132 and a toggle bar 134. The first cable 128 extends over the first pair of pulleys 120a, and the second cable 132 extends over the second pair of pulleys 120b. The first cable 128 has a first end 128a fixedly coupled to the counterweight 130, and a second end (not explicitly shown) fixedly coupled to the carriage 106. Similarly, the second cable 132 has a first end (not explicitly shown) fixedly coupled to the counterweight 130, and a second end (not explicitly shown) fixedly coupled to the carriage 106.

The toggle bar 134 of the pulley assembly 120 is pivotably supported on the counterweight 130. The toggle bar 134 has a first end 134a having the first end 128a of the first cable 128 fixed thereto, and a second end 134b having the first end of the second cable 132 fixed thereto. The toggle bar 134 has an intermediate portion pivotably attached to a fulcrum 136, which is attached to the counterweight 130.

The toggle bar 134 accounts for any manufacturing tolerances or stretching in the cables 128, 132 that may occur over time. For example, if the first cable 128 begins to stretch or lengthen whereas the second cable 132 does not, the toggle bar 134 will pivot to move the first end 134a of the toggle bar 134 toward the counterweight 130 to account for the lengthening of the first cable 128. As such, even with an uneven tension in one of the cables 128, 132, the first and second cables 128, 132 continue to carry an equal load of the counterweight 130. Further, the toggle bar 134 accommodates for manufacturing tolerances in the cables 128a, 132.

With reference to FIG. 6, the counterweight 130 has a mass substantially equal to the combined mass of the carriage 106, the robotic arm 3, and the attached surgical instrument 10. In some embodiments, the counterweight 130 may have a mass substantially equal to the combined mass of the carriage 106, the robotic arm 3, and/or the surgical instrument 10. The counterweight 130 functions to reduce the effort required of a clinician, or in some embodiments, a motor, in raising or lowering the carriage 106 (with the robotic arm 3 attached) along the support column 104 by making the carriage 106 free-floating. As illustrated, the counterweight 130 may include a plurality of discreet weights stacked on one another. Each of the weights may be detachable from the counterweight unit 130 to provide a clinician with the ability to adjust the mass of the counterweight 130 depending on the mass of the carriage 106, the robotic arm 3, and/or other components being ultimately supported by the carriage 106. In embodiments, the counterweight 106 may be considered a component of the pulley assembly 120.

Figure 7:
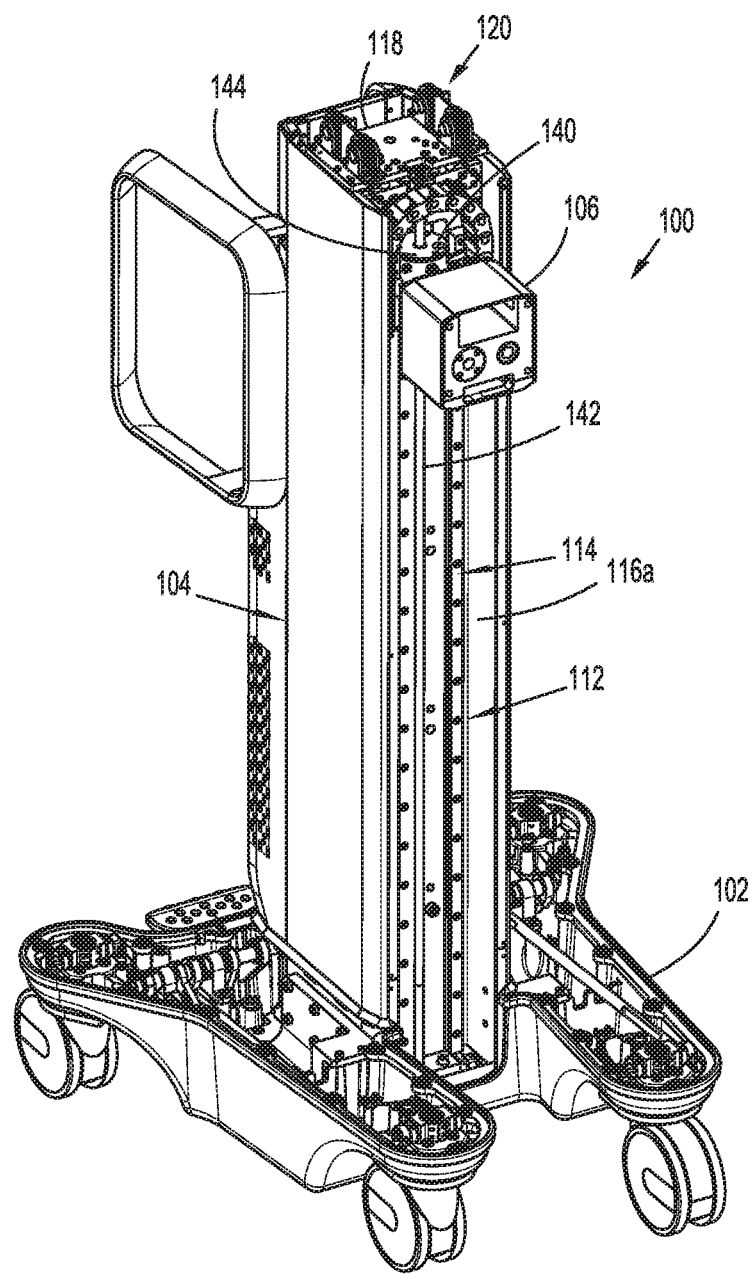
FIG. 7 is a front, perspective view of the surgical cart of FIG. 2.
Figure 8:
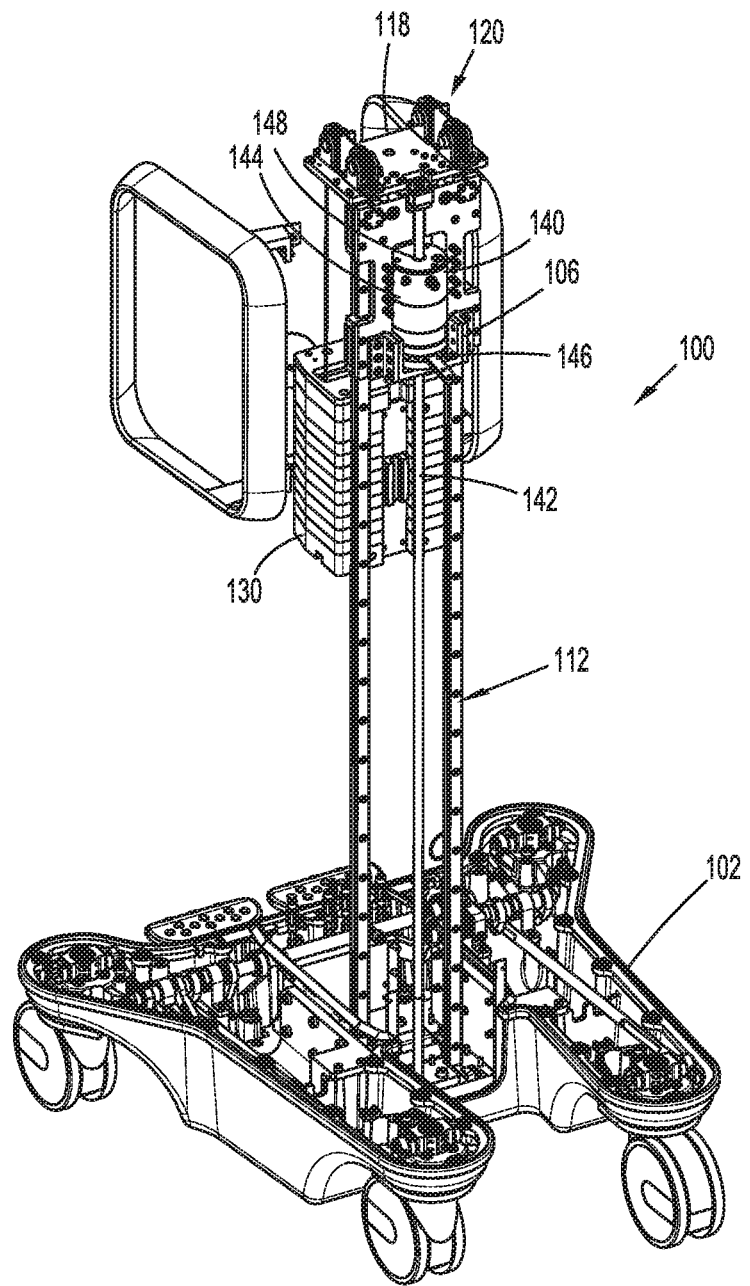
FIG. 8 is a front, perspective view, with parts removed, illustrating a braking mechanism of the surgical cart of FIG. 2.

With reference to FIGS. 7 and 8, the surgical cart 100 includes a braking mechanism 140 disposed within the cavity 112 of the support column 104. The braking mechanism 140 includes a shaft or rod 142 and a brake 144 slidably mounted to the shaft 142. The shaft 142 extends longitudinally within the support column 104 and is fixed at its ends between the platform 118 and the cart base 102.

The brake 144 has a connector or extension 146 that fixes the brake 144 to the carriage 106 such that axial movement of the carriage 106 along the track 116a of the support column 104 causes the brake 144 to slide along the shaft 142. A longitudinally-extending channel 148 is defined through the brake 144 and has the shaft 142 extending therethrough. The brake 144 may be configured as an electromagnetic brake, a servomotor brake, hydraulic, pneumatic, or the like.

In response to an actuation of the brake 144 via the control device 4, the brake 144 frictionally engages the shaft 142. In some embodiments, instead of or in addition to the control device 4 being responsible for actuating the brake 144, the brake 144 may include a sensor (not explicitly shown) that senses a threshold force applied on the carriage 106 causing the brake 144 to automatically release from engagement with the shaft 142. The threshold force sensed by the sensor may be an upward force applied by the clinician on the carriage 106 intended to raise the carriage 106. In embodiments, the brake 144 may automatically frictionally engage the shaft 142 in the absence of the threshold force.

In other embodiments, the sensor may be configured to detect when the motor 126 (FIG. 5) of the pulley assembly 120 is being activated, or may receive a contemporaneous signal from control device 4 indicating that motor 126 is being activated. Upon the sensor sensing an activation of the motor 126 or receiving a signal from control device 4, the brake 144 releases from engagement with the shaft 142 to allow for the raising or lowering of the carriage 106 driven by the motor 126.

Figure 9:
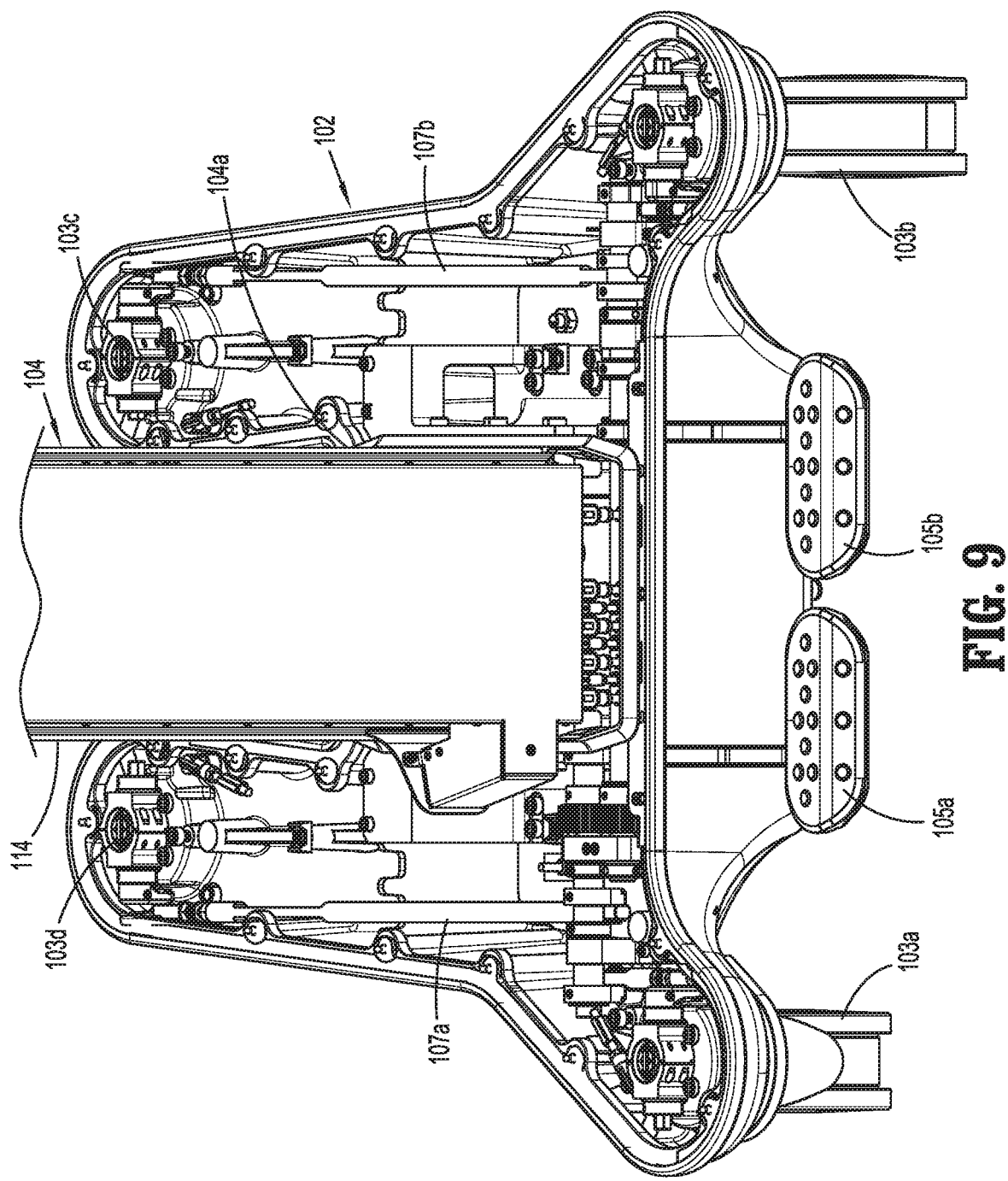
FIG. 9 is an enlarged view of a rolling base of the surgical cart of FIG. 2, with a cover removed therefrom.

With reference to FIG. 9, the cart base 102 of the surgical cart 100 is fixed to the first end 104a of the support column 104 and includes four casters 103a, 103b, 103c, 103d. In some embodiments, the cart base 102 may include more or less than four casters. The cart base 102 further includes two foot pedals 105a, 105b coupled to the casters 103a-103d via linkages 107a, 107b that function to rotate the casters 103a-103d in a selected direction. As such, using the foot pedals 105a, 105b, a clinician may control the direction of movement of the surgical cart 100.

In operation, with a robotic arm 3 supported on the carriage 106, the carriage 106 may be raised or lowered to a selected vertical position along the longitudinal axis "X" of the support column 104. For example, to raise the carriage 106, and in turn the robotic arm 3, a clinician may either actuate the motor 126 in the hubs 122a, 122b of the pulley assembly 120 via the control device 4, or manually raise the carriage 106 by hand. In either scenario, the counterweight 130 of the pulley assembly 120 reduces the energy or force required to raise the carriage 106 due to the counterweight 130 acting on the carriage 106 in the same direction that the carriage 106 is being moved by the clinician or the motor 126.

Upon the clinician ceasing application of the upward force on the carriage 106, the brake 144 of the braking mechanism 140 automatically (e.g., via the sensor) frictionally engages the shaft 142 of the braking mechanism 140, thereby halting further vertical movement, in either direction, of the carriage 106 along the support column 104. Similarly, in the scenario where the motor 126 of the pulley assembly 120 is used to adjust the height of the carriage 106, upon the motor 126 ceasing to rotate the pulleys 120a, 120b, the brake 144 of the braking mechanism 140 is automatically actuated (e.g., via the sensor) to engage the shaft 142 of the braking mechanism 140, thereby halting further vertical movement of the carriage 106 along the support column 104 in either direction. In embodiments, the brake 144 may have a manual override in case of a power failure.

With the brake 144 engaged to the shaft 142, the carriage 106 will be fixed in its vertical position on the support column 104. In the instance where the combined mass of the carriage 106, the robotic arm 3, and the surgical instrument 10 is greater than the mass of the counterweight 130, the brake 144 will prevent the carriage 106 from being lowered so long as the brake 144 is in the actuated state. In the alternative instance where the counterweight 130 is greater in mass than the combined mass of the carriage 106, the robotic arm 3, and the surgical instrument 10, the brake 144 will prevent the carriage 106 from being raised so long as the brake 144 is in the actuated state.

Figure 10:
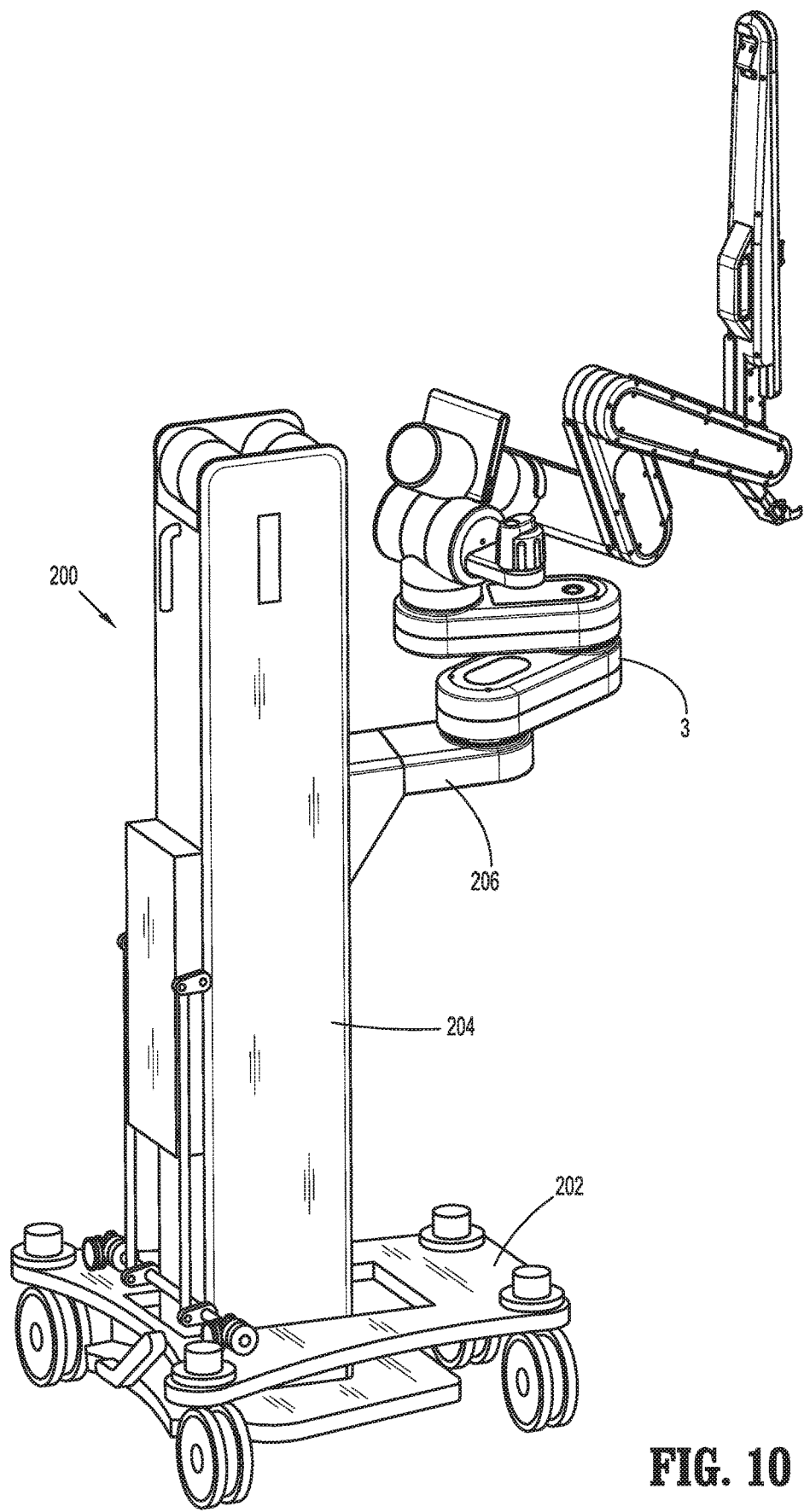
FIG. 10 is a perspective view of another embodiment of a surgical cart having a robotic arm attached thereto.
Figure 11:
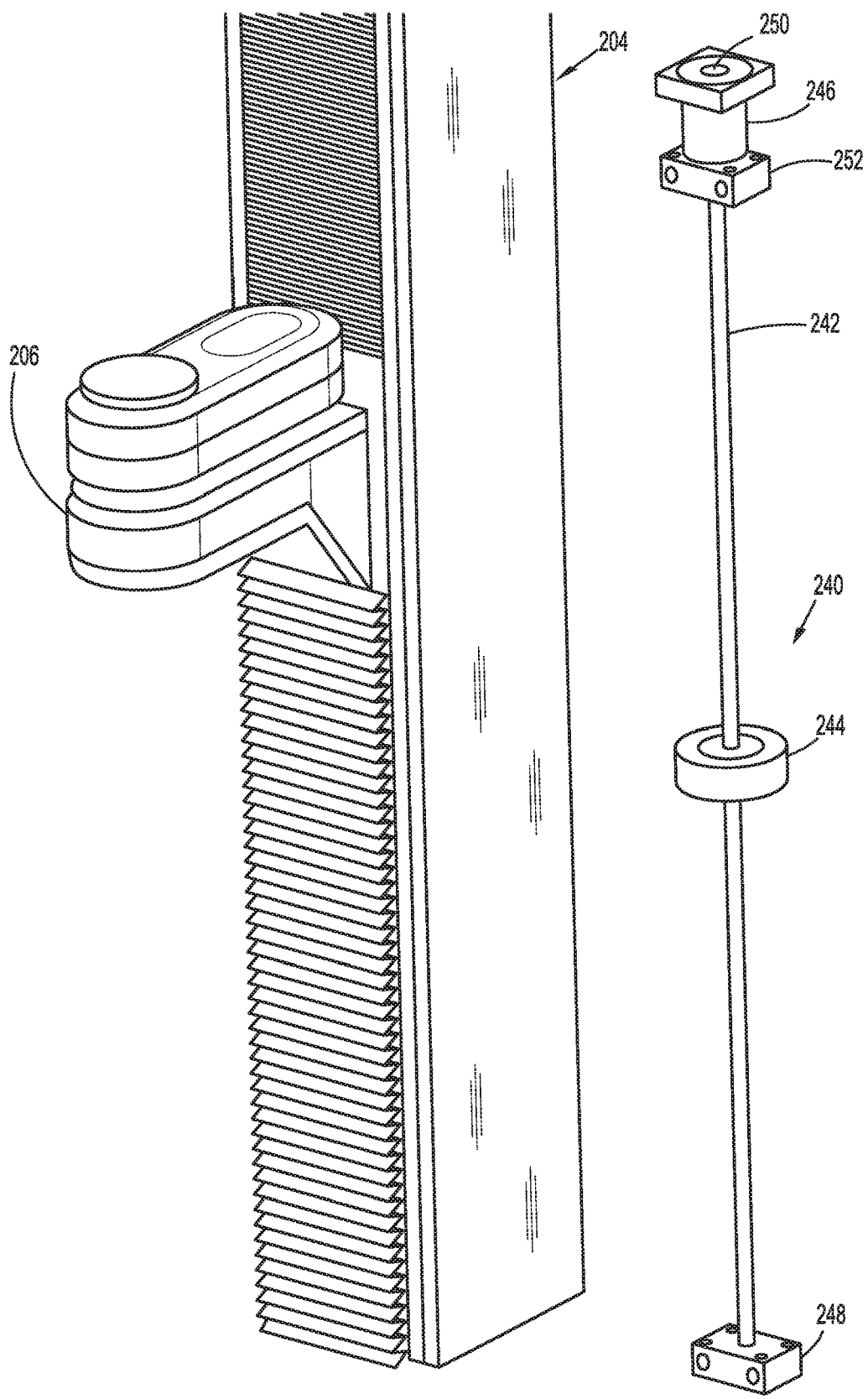
FIG. 11 is a perspective view, with some parts separated, of a support column of the surgical cart of FIG. 10 and a braking mechanism thereof.

With reference to FIGS. 10 and 11, illustrated is another embodiment of a surgical cart 200 of the robotic surgical system 1 configured for use in accordance with the present disclosure. The surgical cart 200 is configured to move the robotic arm 3 to a selected position within operating room "OR" (FIG. 1) and to provide vertical movement of the robotic arm 3. The surgical cart 200 generally includes a cart base 202, a support column 204 extending vertically (e.g., perpendicularly) from the cart base 202, and a carriage or slider 206 configured for supporting the robotic arm 3 thereon. Only those components of the surgical cart 200 deemed important in elucidating features that differ from the surgical cart 100 of FIGS. 2-9 will be described in detail.

The surgical cart 200 includes a braking mechanism 240 for selectively fixing the vertical position of the carriage 206, and in turn the robotic arm 3, relative to the support column 204. In one embodiment, the braking mechanism 240 includes a ball screw assembly 242, 244 and a motorized brake 246 operably engaged to the ball screw assembly. The ball screw assembly includes a ball screw 242 and a ball nut 244 threadingly coupled to the ball screw 242. In embodiments, instead of the braking mechanism 240 having a ball screw assembly, the braking mechanism 240 may include a conventional lead screw and a conventional nut threaded thereto. The ball screw 242 has a high pitch relative to a conventional ball screw, wherein the relative high pitch facilitates raising and lowering of carriage 106, and in turn, robotic arm 3.

The ball nut 244 of the braking mechanism 240 is rotatably mounted to the carriage 206 such that the nut 244 moves with the carriage 206 axially along the length of the support column 204. It is contemplated that the nut 244 may have a surface feature (not explicitly shown) defined on its outer surface that engages with a corresponding surface feature (not explicitly shown) on the carriage 206 which allows for relative rotation of the nut 244 while inhibiting relative axial movement of the nut 244. The nut 244 is threadingly coupled to the ball screw 242 such that axial movement of the nut 244 along the ball screw 242 causes the ball screw 242 to rotate about its longitudinal axis. The ball screw 242 of the braking mechanism 240 extends longitudinally within the support column 204 and is axially fixed at its ends between a platform 248 and the brake 246 of the braking mechanism 240.

The brake 246 of the braking mechanism 240 is mounted on the end of the ball screw 242 and may be an electromagnetic brake, a servomotor brake, or the like. The brake 246 defines a longitudinally-extending channel 250 having the end of the ball screw 242 extending therethrough. The brake 246 is configured to selectively frictionally engage the ball screw 242 in response to an actuation of the brake 246 via the control device 4. In some embodiments, instead of or in addition to the control device 4 being responsible for actuating the brake 246, the brake 246 may include a sensor (not explicitly shown) that controls the actuation of the brake 246. In particular, the sensor may be configured to sense a threshold force applied on the carriage 206 and in response cause the brake 246 to automatically release from engagement with the ball screw 242. The threshold force sensed by the sensor may be caused by a clinician applying an upward force on the carriage 206 intended to raise the carriage 206. The brake 246 may be further configured to automatically frictionally engage the ball screw 242 in the absence of the threshold force. As such, the sensor controls the brake 246 of the braking mechanism 240 for selectively fixing the vertical position of the carriage 206 on the support column 204. As can be appreciated, a processor (not explicitly shown) may be provided to direct the operation of the brake 246 in response to the sensor sensing the threshold force.

In some embodiments, the surgical cart 200 may further include a motor 252 operably coupled to the ball screw 242 to effect a rotation of the ball screw 242. In this embodiment, an activation of the motor 252 causes the ball screw 242 to rotate, thereby driving an upward or downward movement of the nut 244 along the ball screw 242 and, in turn, a corresponding upward or downward movement of the carriage 206. In other embodiments, the sensor may be configured to detect when the motor 252 is being activated and upon the sensor sensing the activation of the motor 252, the brake 246 may be configured to automatically release from engagement with the ball screw 242 to allow for the raising or lowering of the carriage 206 by the motor 252. In still other embodiments, another brake (not shown) may be provided that selectively engages the nut 244 to prevent rotation of the nut 244 and/or axial translation of the nut 244.

In operation, to raise or lower the robotic arm 3, a clinician may either manually apply a force on the carriage 206, or the motor 252 may be activated by a clinician pressing a button to drive the carriage 206 movement. The sensor senses either the manual force being applied on the carriage 206, or the sensor senses an activation of the motor 252. The sensor communicates with the processor, which then directs the brake 246 of the braking mechanism 240 to release the ball screw 242. If vertical adjustment of the carriage 206 is being driven manually, the force applied on the carriage 206 by the clinician moves the carriage 206 and the attached nut 244 and robotic arm 3, along the ball screw 242 since the ball screw 242 is no longer being prevented from rotating by the brake 246. If vertical adjustment of the carriage 206 is being driven by the motor 252, the activation of the motor 252 rotates the ball screw 242 since the ball screw 242 is no longer being prevented from rotating by the brake 246. As the ball screw 242 rotates, the nut 244 moves along the ball screw 242, thereby moving the carriage 206 and the attached robotic arm 3 along the support column 204.

Figure 12:
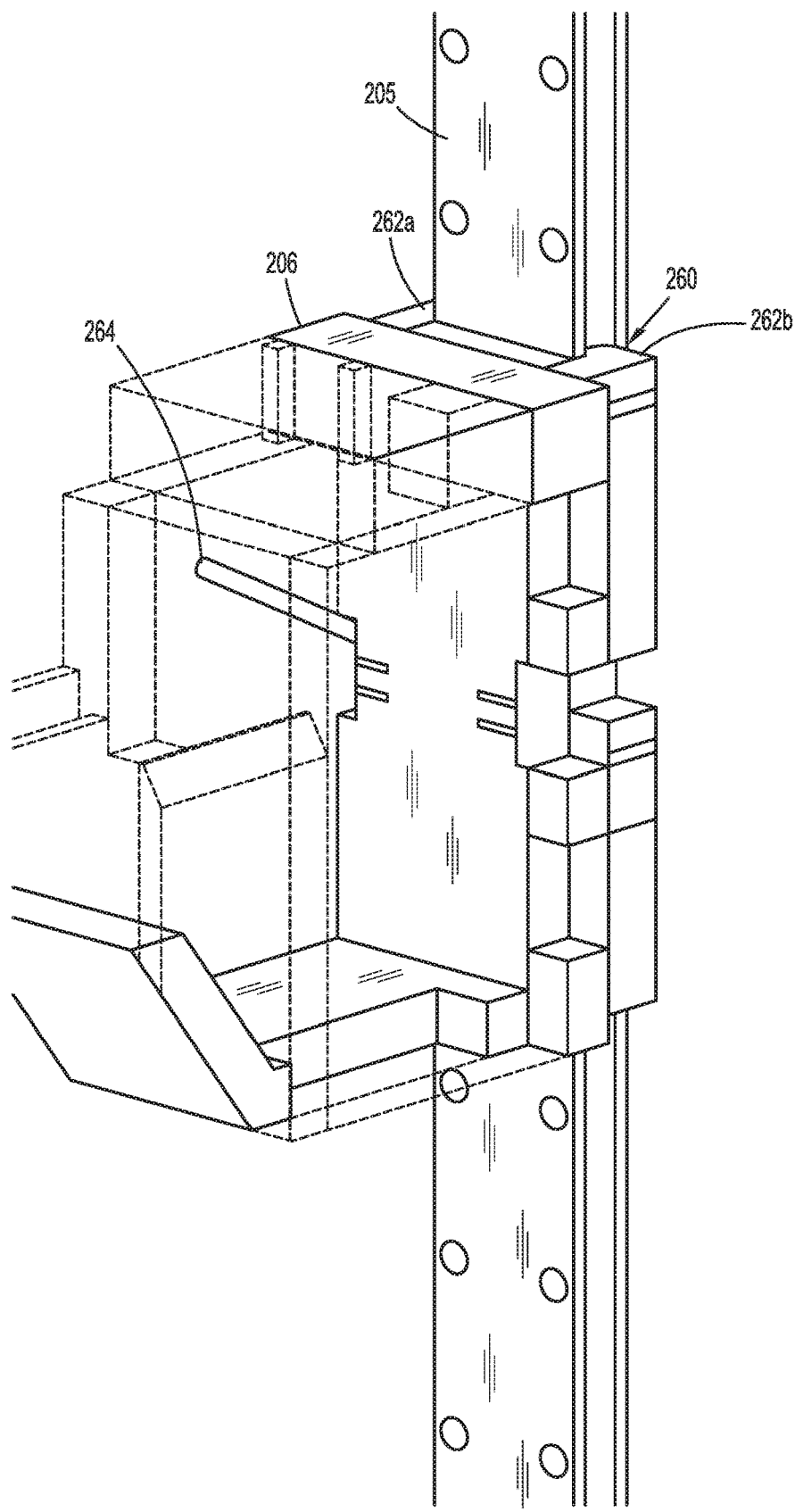
FIG. 12 is a perspective view of another embodiment of a braking mechanism for use with the surgical cart of FIG. 10.
Figure 13:
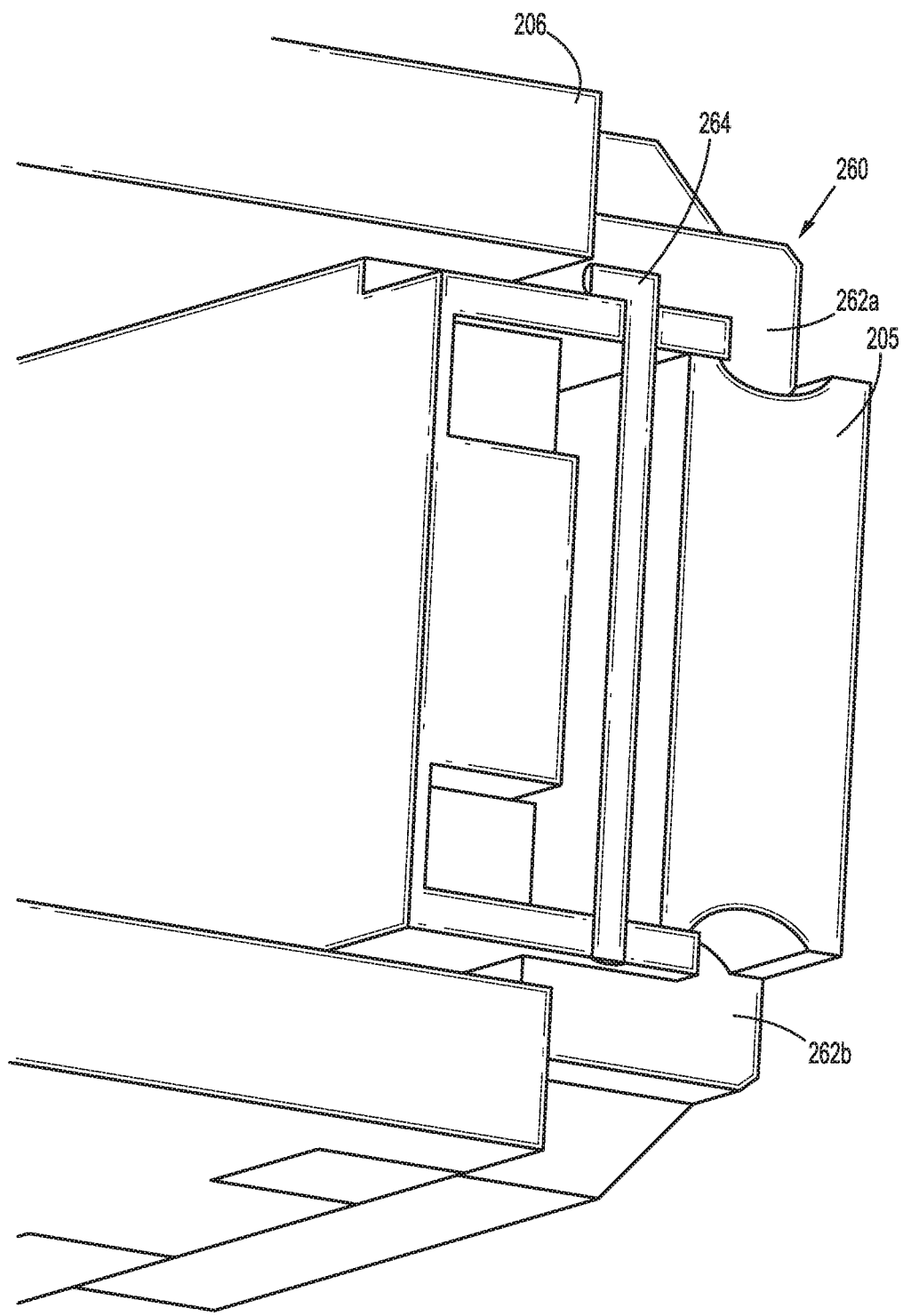
FIG. 13 is an enlarged view of the braking mechanism of FIG. 12 shown attached to a rail of the surgical cart.
Figure 14:
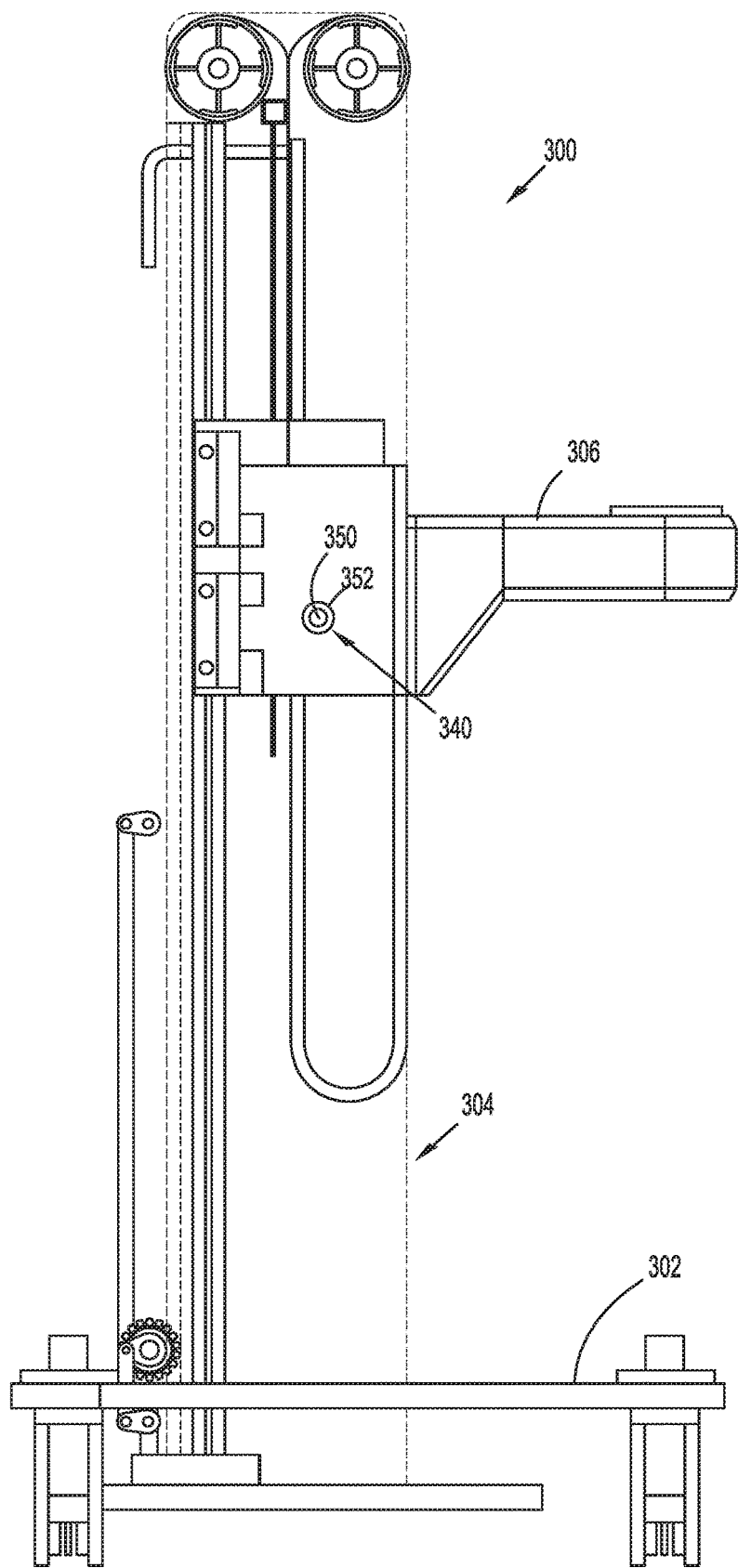
FIG. 14 is a first side view of the surgical cart of FIG. 10.
Figure 15:
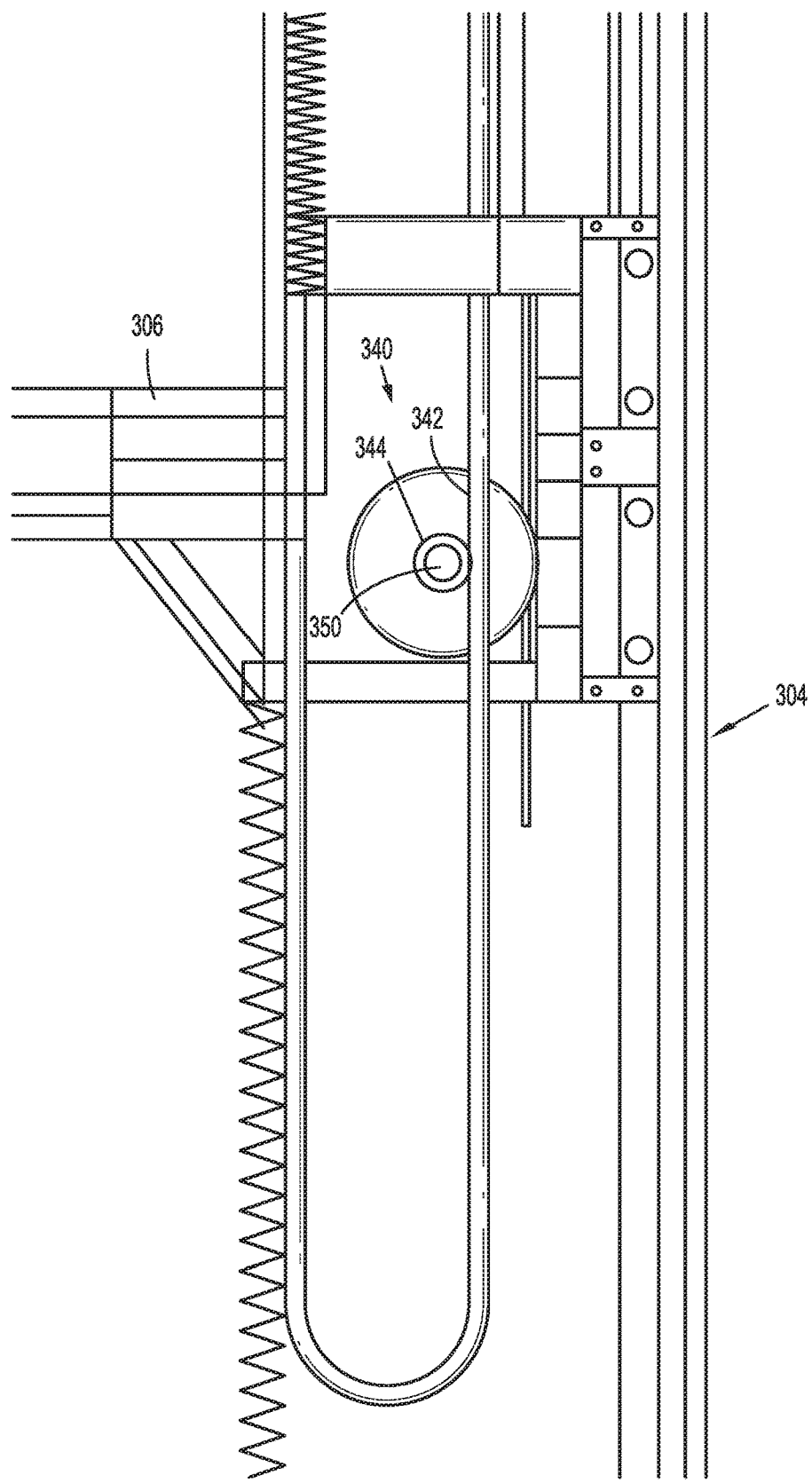
FIG. 15 is an enlarged, second side view of the surgical cart of FIG. 10 illustrating another embodiment of a braking mechanism.
Figure 16:
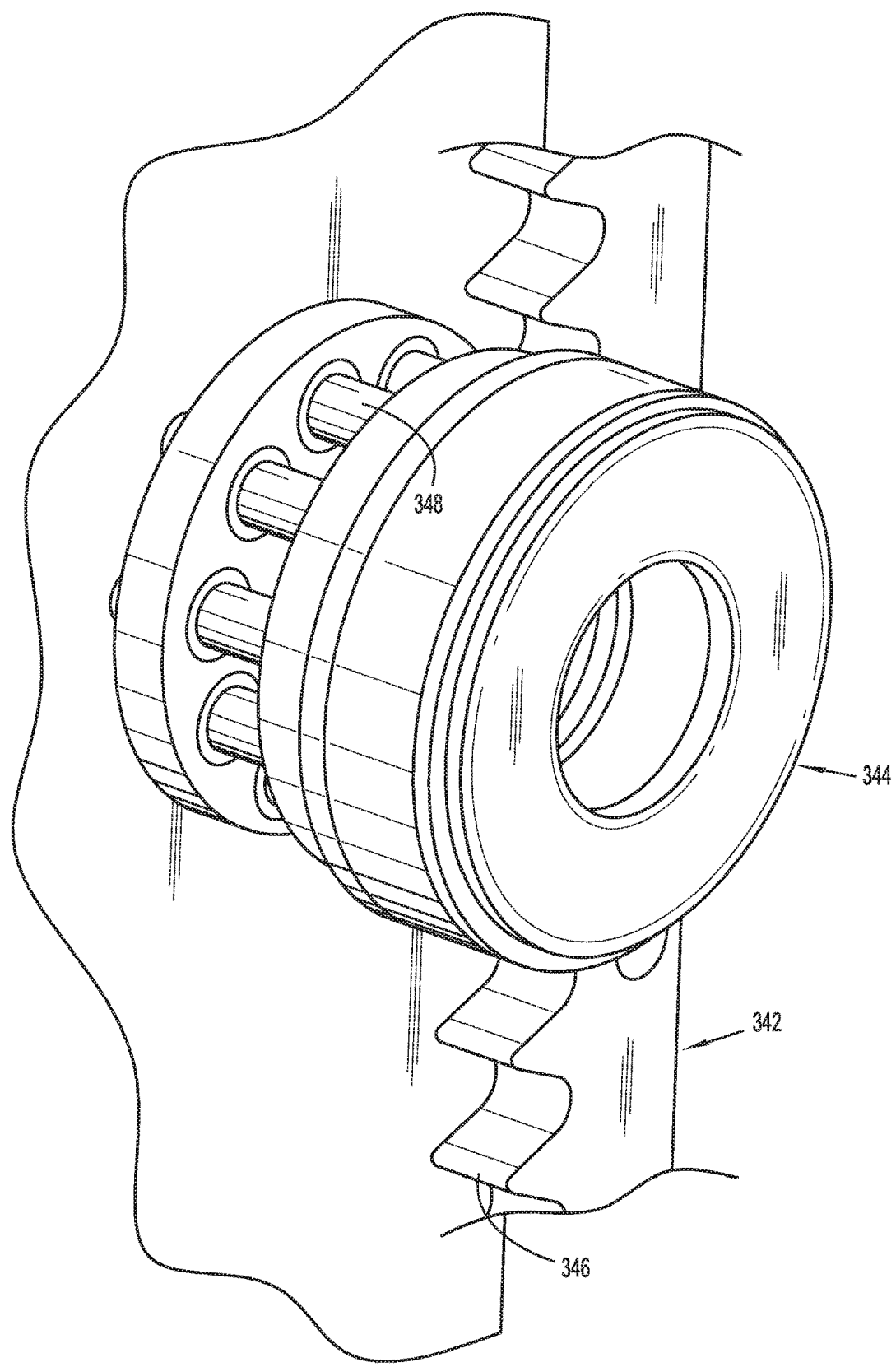
FIG. 16 is an enlarged view of a rack and pinion of the braking mechanism of FIG. 15.
Figure 17:
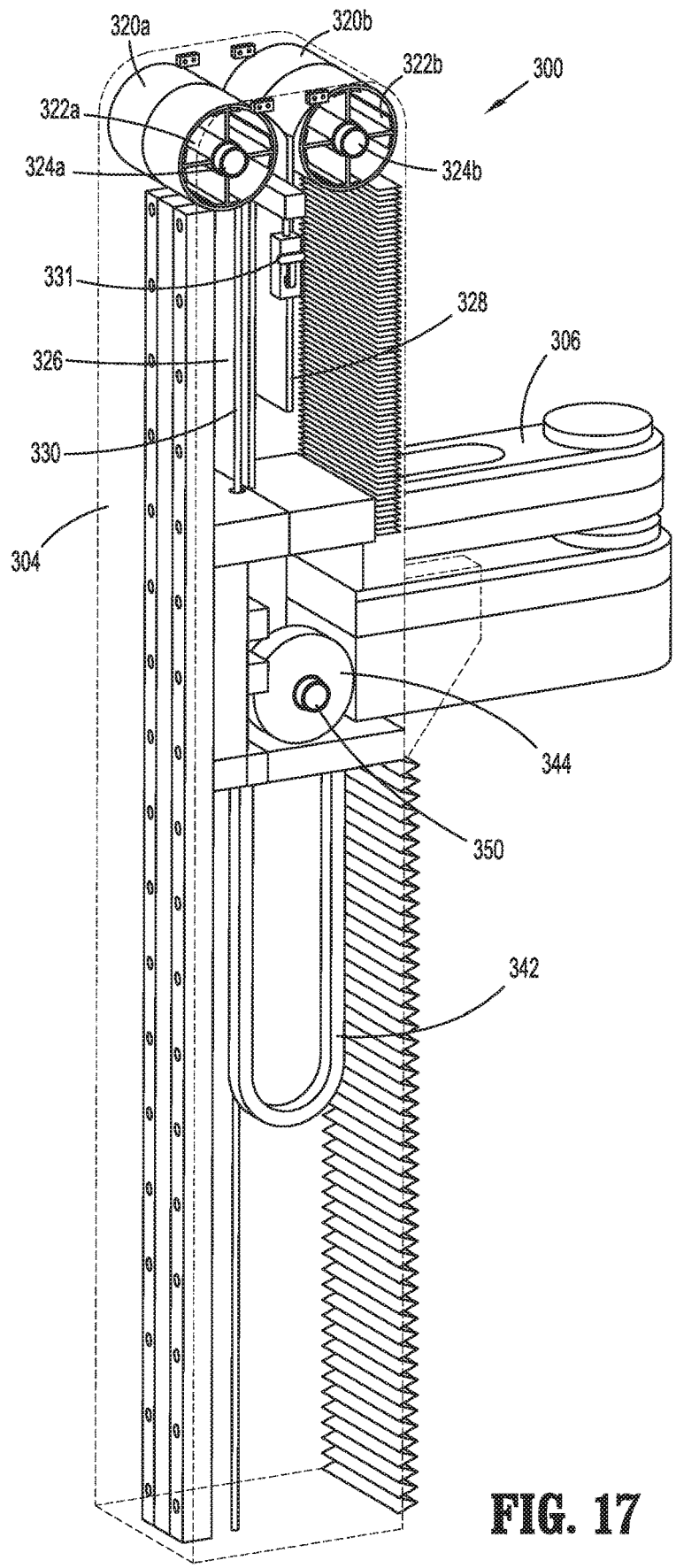
FIG. 17 is a perspective view of the surgical cart of FIG. 10 illustrating a spring-based counterbalance mechanism.

With reference to FIGS. 12 and 13, illustrated is another embodiment of a braking mechanism 340 for use with the surgical cart 200 of the robotic surgical system 1. The braking mechanism 260 includes a linear motion brake mounted to the carriage 206 and movable therewith. The linear motion brake includes a pair of clamp arms 262a, 262b that selectively grasp a track 205 of the support column 204 to halt axial movement of the carriage 206 along the track 205. The linear motion brake may include a manual actuator 264 operable by a clinician to manually actuate the linear brake. A detail description of an exemplary linear motion brake may be found in U.S. Pat. No. 8,220,592.

With reference to FIGS. 14-20, illustrated is another embodiment of a surgical cart 300 of robotic surgical system 1 configured for use in accordance with the present disclosure. The surgical cart 300 is configured to move the robotic arm 3 to a selected position within the operating room "OR" (FIG. 1) and to provide vertical movement of the robotic arm 3. The surgical cart 300 generally includes a cart base 302, a support column 304 extending vertically (e.g., perpendicularly) from the cart base 302, and a carriage or slider 306 configured for supporting the robotic arm 3 thereon. Only those components of the surgical cart 300 deemed important in elucidating features that differ from the surgical cart 100 of FIGS. 2-9 will be described in detail.

The surgical cart 300 includes a braking mechanism 340, similar to the braking mechanism 240 described with reference to FIG. 11. The braking mechanism 340 is configured to fix the vertical position of the carriage 306, and in turn the robotic arm 3, relative to the support column 304. The braking mechanism 340 includes a rack 342 and pinion 344 operably coupled to one another to selectively halt axial movement of the carriage 306 along the support column 304.

The rack 342 of the braking mechanism 340 is fixedly mounted to the support column 304 and extends parallel with the longitudinal axis of the support column 304. The rack 342 defines a plurality of teeth 346 along its length configured to meshingly engage with bars 348 of the pinion 344. The pinion 344 of the braking mechanism 340 is non-rotatably mounted to an axle 350 that is rotatably mounted to the carriage 306. As such, the pinion 344 is able to rotate relative to the carriage 306 while being axially fixed relative to the carriage 306. In some embodiments, the axle 350 is rotatably fixed relative to the carriage 306 while the pinion 344 is rotatably mounted to the axle 350. In some embodiments, the pinion 344 may have helical teeth for reducing backlash.

The braking mechanism 340 further includes a brake 352 mounted to an end of the axle 350. The brake 352 may be an electromagnetic brake, a servomotor brake, or the like, and is configured to selectively frictionally engage the pinion 344 in response to an actuation of the brake 344 via the control device 4. In some embodiments, instead of or in addition to the control device 4 being responsible for actuating the brake, the brake 344 may include a sensor (not explicitly shown) that controls the actuation of the brake 344. In particular, the sensor may be configured to sense a threshold force applied on the carriage 306 and in response cause the brake 352 to automatically release from engagement with the pinion 344. The threshold force sensed by the sensor may be caused by a clinician applying an upward force on the carriage 306 intended to raise the carriage 306. The brake 352 may be further configured to automatically frictionally engage the pinion 344 in the absence of the threshold force. As such, the sensor controls the brake 352 of the braking mechanism 340 for selectively fixing the vertical position of the carriage 306 on the support column 304. As can be appreciated, a processor, e.g., the control device 4, may be provided to direct the operation of the brake 352 in response to the sensor sensing the threshold force.

The support column 304 may further include a motor (not explicitly shown) operably coupled to the pinion 344 or the axle 350 to effect a rotation of the pinion 344 either directly, or indirectly via the axle 350. In this embodiment, an activation of the motor causes the pinion 344 to rotate, thereby driving an upward or downward movement of the pinion 344 along the rack 342, and in turn, a corresponding upward or downward movement of the carriage 306 along the support column 304. In other embodiments, the sensor may be configured to detect when the motor is being activated and upon the sensor sensing an activation of the motor, the brake 352 may automatically release from engagement with the pinion 344 to allow for the raising or lowering of the carriage 306. As can be appreciated, the processor may be configured to direct the operation of the brake 352 in response to the sensor sensing an activation or deactivation of the motor.

In one embodiment, both the axle 350 and the pinion 344 may be non-rotatable relative to the carriage 306. In this embodiment, the pinion 344 is movable between a first or braking position in which the pinion 344 is engaged to the rack 342, and a second or non-braking position in which the pinion 344 is disengaged from the rack 342. As such, the pinion 344 acts as the brake 352 by being selectively engaged with the rack 342 to halt movement of the carriage 306 along the support column 304.

In operation, to raise or lower the robotic arm 3, a clinician may either manually apply a force on the carriage 306, or the motor may be activated to drive the carriage 306 movement. The sensor senses either the manual force being applied on the carriage 306 by the clinician, or the sensor senses an activation of the motor. The sensor communicates with the processor, which then directs the brake 352 of the braking mechanism 340 to release the pinion 344. If vertical adjustment of the carriage 306 is being driven manually, the force applied on the carriage 306 by the clinician moves the carriage 306, the attached robotic arm 3, and the pinion 344, along the support column 304 since the pinion 344 is no longer being prevented from rotating by the brake 352. If vertical adjustment of the carriage 306 is being driven by the motor, the activation of the motor rotates the pinion 344 since the pinion 344 is no longer being prevented from rotating by the brake 352. As the pinion 344 rotates, the pinion 344 moves axially along the rack 342, thereby moving the carriage 306 and the attached robotic arm 3 along the support column 304.

With reference to FIGS. 17-20, the surgical cart 300 includes a pair of spring members 320a, 320b mounted in the support column 304 and configured to counterbalance the combined mass of the carriage 306 and the attached robotic arm 3. Each of the spring members 320a, 320b may be constant force springs having one or more laminations or layers fabricated from stainless steel, fiberglass, or any suitable material. The number and thickness of the laminations and the type of material used to fabricate the constant-force springs 320a, 320b is selected based on the combined mass of the carriage 306, the robotic arm 3, and the attached surgical instrument.

Figure 18:
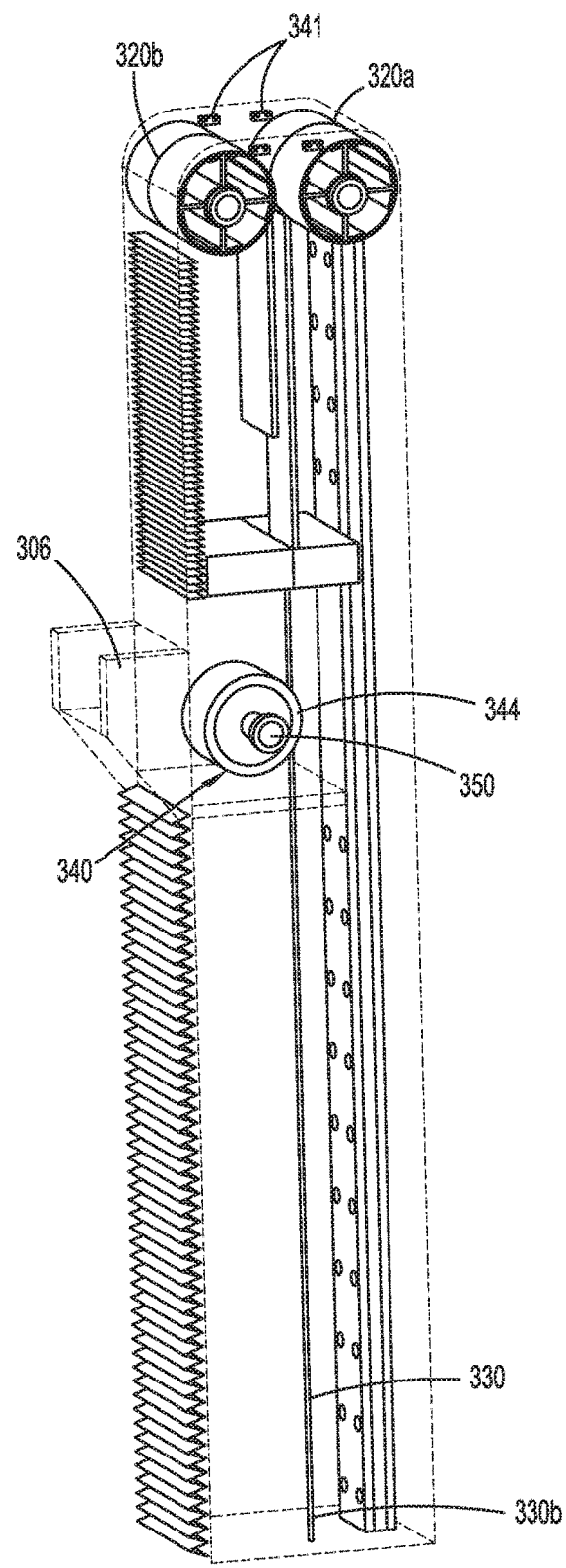
FIG. 18 is another perspective view of the surgical cart of FIG. 10.
Figure 19:
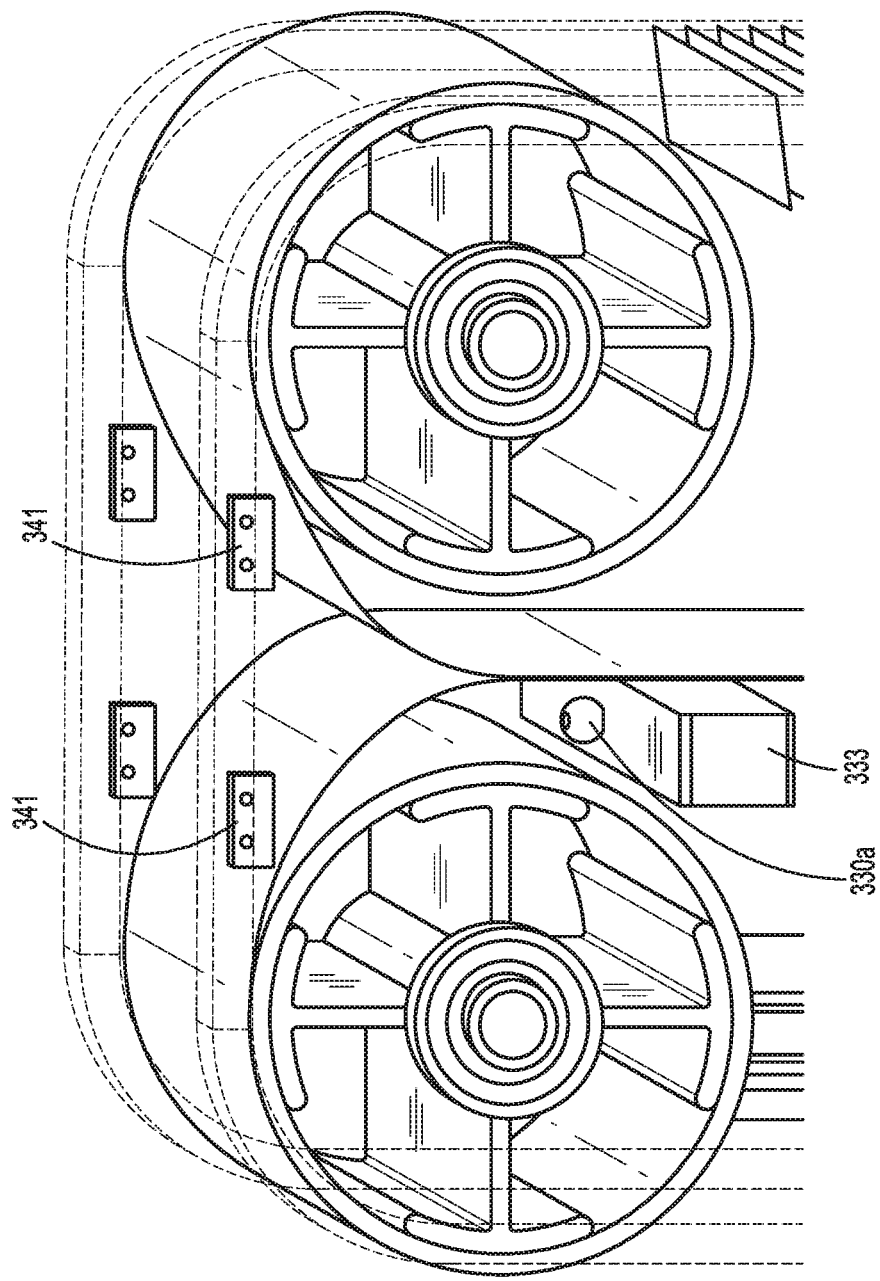
FIG. 19 is an enlarged view of components of the spring-based counterbalance mechanism of FIG. 17.

The constant-force springs 320a, 320b are each coiled about a drum 322a, 322b. The two drums 322a, 322b are disposed adjacent one another and are each rotatably mounted to a respective axle or pivot pin 324a, 324b. A first end of each of the springs is secured (e.g., bolted or soldered) to the respective drum 322a, 322b, and a second end 326, 328 of each of the springs 320a, 320b extends downwardly from the respective drum 322a, 322b. One or both of the second ends 326, 328 of the springs 320a, 320b are directly attached to the carriage 306. The springs 320a, 320b function to reduce the effort required of a clinician, or in some embodiments, a motor, in raising or lowering the carriage 306 (with the robotic arm 3 attached) along the support column 304 by making the carriage 306 free-floating. As shown in FIGS. 18 and 19, electrical switches 341, such as, for example, hall effect sensors, may be associated with the springs 320a, 320b used to detect if the springs 320a, 320b break. Specifically, if and spring 320a, 320b should break, the respective electrical switch 341 would be activated, thereby providing a signal or the like to the clinician or technician that there has been a failure, and, in embodiments, the system is placed in a permanent or temporary "hold" or "shut-down" state, until the particular robotic cart 300 is replaced and/or repaired.

In operation, with a robotic arm 3 supported on the carriage 306, the carriage 306 may be raised or lowered to a selected position along the longitudinal axis of the support column 304. For example, to lower the carriage 306, a threshold amount of force is required to overcome the spring force of the springs 320a, 320b. Upon overcoming the spring force of the springs 320a, 320b, the carriage 306 is lowered away from the drums 322a, 322b, thereby uncoiling the springs 320a, 320b. A brake, such as, for example, the braking mechanism 340, may be used to maintain the carriage 306 in the selected vertical position on the support column 304.

To raise the carriage 306 from the lowered position, the brake is released allowing the spring force of the springs 320a, 320b to act on the carriage 306. As the springs 320a, 320b attempt to return to their natural, coiled state, the springs 320a, 320b exert an upwardly-oriented force on the carriage 306 to facilitate upward vertical movement of the carriage 306 along the support column 304. As such, the springs 320a, 320b reduce the energy required to raise the carriage 306 due to the springs 320a, 320b acting on the carriage 306 in the same direction the carriage 306 is being moved by the clinician or the motor.

Figure 20:
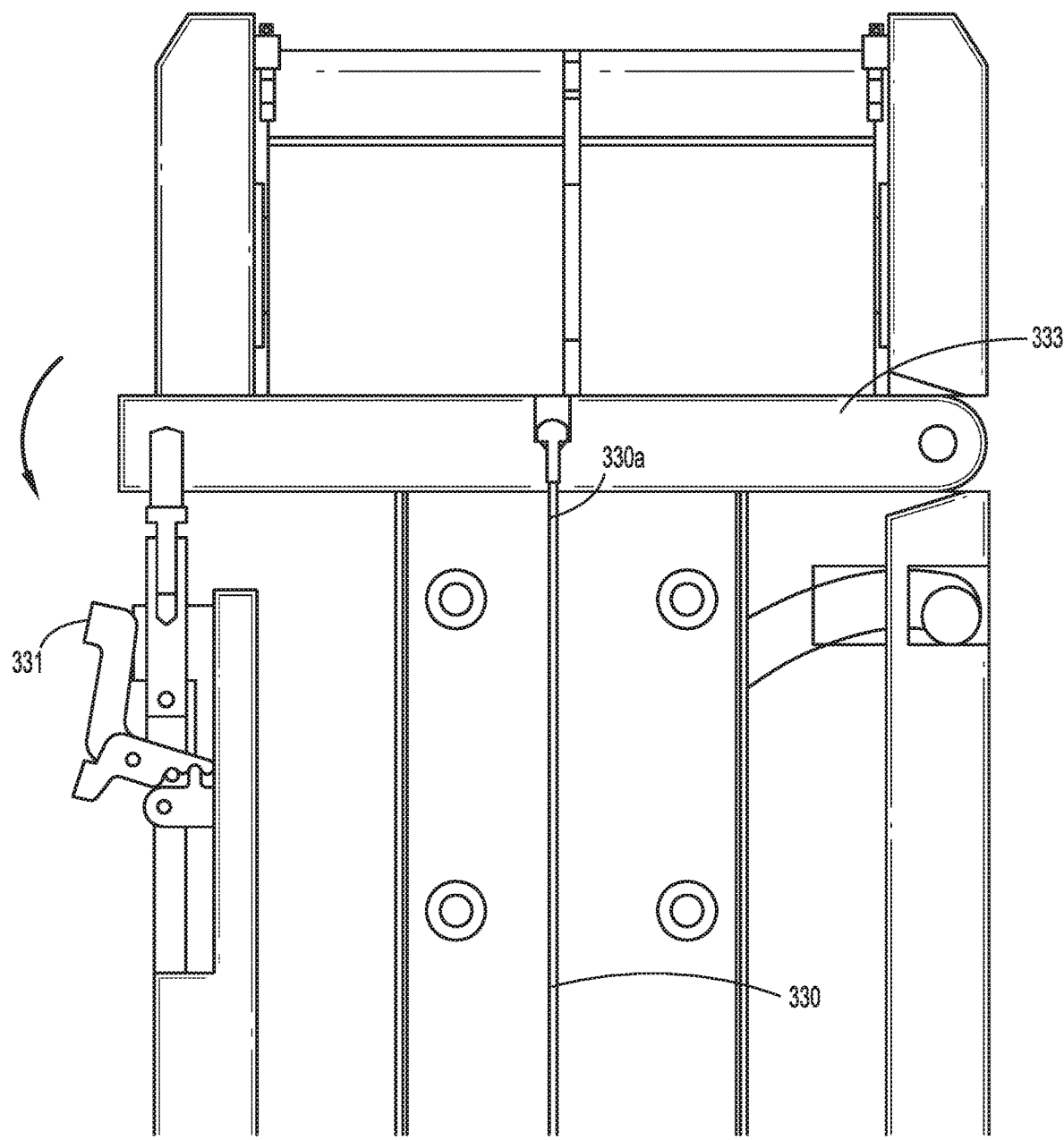
FIG. 20 is a rear view of the counterbalance mechanism of FIG. 17.

With continued reference to FIGS. 17-20, the cart 300 may further include an overlatch mechanism for adjusting the force required to rotate the pinion 344 of the braking mechanism 340. In particular, the overlatch mechanism includes a cable 330, a lever 331, and a pivot arm 333 (FIG. 20). The cable 330 has a first end 330a anchored to the lever 331, and a second end 330b anchored to a base of the support column 304. The cable 330 is wrapped about the pinion 344 of the braking mechanism 340 to provide a selective amount of resistance to rotation of the pinion 344. For example, the tighter the cable 330 is wrapped about pinion 344, the more force is required to rotate pinion 344 and, in turn, move the carriage 306 along the axis of the support column 304. To lower the tension in the cable 330, the lever 331 is actuated, which causes the pivot arm 333 to pivot downwardly, thereby bringing the first end 330a of the cable 330 closer to the second end 330b. In this way, the cable 330 loosens about the pinion 344 to allow the pinion 344 to more easily rotate.

It is contemplated that the surgical carts 100, 200, 300 of the present disclosure may incorporate any of the braking mechanisms described above for holding the carriage in a selected vertical position along the support column.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A surgical cart for supporting a robotic arm, comprising:
   a vertically-extending support column;
   a carriage movably coupled to the support column and configured to carry a robotic arm; and
   a braking mechanism including:
      a screw defining a longitudinal axis and rotatably supported in the support column;
      a nut threaded to the screw and coupled to the carriage such that axial translation of the carriage and in turn the nut along the screw causes the screw to rotate about the longitudinal axis defined by the screw; and
      a brake configured to selectively engage the screw to prevent rotation of the screw and in turn axial movement of the nut and the carriage along the longitudinal axis defined by the screw.

2. The surgical cart according to claim 1, wherein the screw is a ball screw and the nut is a ball nut.

3. The surgical cart according to claim 1, wherein the brake is configured to move relative to the screw between a first position in which the screw is permitted to rotate, and a second position, in which the brake prevents the screw from rotating relative to the nut.

4. The surgical cart according to claim 1, further comprising a pulley assembly including:
   a first pulley supported on the support column;
   a first cable extending over the first pulley and having a first end fixed to the carriage and a second end; and
   a counterweight fixed to the second end of the first cable.

5. The surgical cart according to claim 4, wherein the pulley assembly includes:
   a second pulley supported on the support column; and
   a second cable extending over the second pulley and having a first end fixed to the carriage and a second end fixed to the counterweight.

6. The surgical cart according to claim 5, wherein the pulley assembly includes a toggle bar pivotably coupled to the counterweight, the toggle bar including a first end having the second end of the first cable fixed thereto, and a second end having the second end of the second cable fixed thereto.

7. The surgical cart according to claim 4, wherein the counterweight includes a plurality of discreet weights in a stacked configuration and detachable from one another.

8. A surgical cart for supporting a robotic arm, comprising:
   a vertically-extending support column;
   a carriage movably coupled to the support column and configured to carry a robotic arm; and
   a braking mechanism disposed within the support column and including:
      a shaft defining a longitudinal axis and extending longitudinally within the support column; and
      a brake fixedly coupled to the carriage and axially movable along the shaft, wherein the brake is configured to selectively engage the shaft to prevent axial movement of the brake and the carriage along the longitudinal axis defined by the shaft.

9. The surgical cart according to claim 8, wherein the brake defines a longitudinally-extending channel having the shaft extending therethrough, the brake configured to selectively frictionally engage the shaft.

10. The surgical cart according to claim 8, further comprising a pulley assembly including:
    a first pulley supported on the support column;
    a first cable extending over the first pulley and having a first end fixed to the carriage and a second end; and
    a counterweight fixed to the second end of the first cable.

11. The surgical cart according to claim 10, wherein the pulley system includes:
    a second pulley supported on the support column; and
    a second cable extending over the second pulley and having a first end fixed to the carriage and a second end fixed to the counterweight.

12. The surgical cart according to claim 11, wherein the pulley system includes a toggle bar pivotably coupled to the counterweight, the toggle bar including a first end having the second end of the first cable fixed thereto, and a second end having the second end of the second cable fixed thereto.

13. The surgical cart according to claim 10, wherein the counterweight includes a plurality of discreet weights in a stacked configuration and detachable from one another.

14. The surgical cart according to claim 8, further comprising a pair of constant-force springs mounted in the support column, wherein each constant-force spring has an end coupled to the carriage such that the pair of constant-force springs exert an upwardly-oriented force on the carriage.

15. The surgical cart according to claim 14, further comprising a cable connecting the end of at least one of the pair of constant-force springs with the carriage.

16. A surgical cart for supporting a robotic arm, comprising:
    a vertically-extending support column defining a longitudinal axis;
    a carriage movably coupled to the support column and configured to carry a robotic arm; and
    a braking mechanism including:
       a rack fixed to the support column; and
       a pinion mounted to the carriage and configured to operably couple to the rack such that axial movement of the carriage along the longitudinal axis defined by the support column is prevented in response to a ceasing of rotation of the pinion.

17. The surgical cart according to claim 16, wherein the braking mechanism includes a brake coupled to the pinion and configured to move relative to the pinion between a first position in which the pinion is permitted to rotate, and a second position, in which the brake prevents the pinion from rotating relative to the brake.

18. The surgical cart according to claim 16, wherein the pinion is non-rotatably coupled to the carriage and is selectively movable relative to the rack between a first position in which the pinion is operably coupled to the rack, and a second position in which the pinion is disengaged from the rack.

19. The surgical cart according to claim 16, further comprising a pulley assembly including:
 a first pulley supported on the support column;
 a first cable extending over the first pulley and having a first end fixed to the carriage and a second end; and
 a counterweight fixed to the second end of the first cable.

20. The surgical cart according to claim 19, wherein the pulley assembly includes:
 a second pulley supported on the support column;
 a second cable extending over the second pulley and having a first end fixed to the carriage and a second end fixed to the counterweight.

21. The surgical cart according to claim 20, wherein the pulley assembly includes a toggle bar pivotally coupled to the counterweight, the toggle bar including a first end having the second end of the first cable fixed thereto, and a second end having the second end of the second cable fixed thereto.

22. The surgical cart according to claim 19, wherein the counterweight includes a plurality of discreet weights in a stacked configuration and detachable from one another.

23. The surgical cart according to claim 16, further comprising a pair of constant-force springs mounted in the support column, wherein each constant-force spring has an end coupled to the carriage such that the pair of constant-force springs exert an upwardly-oriented force on the carriage.

24. The surgical cart according to claim 23, further comprising a cable connecting the end of at least one of the pair of constant-force springs with the carriage.

* * * * *